(12) United States Patent
McKinnon et al.

(10) Patent No.: US 8,496,629 B2
(45) Date of Patent: Jul. 30, 2013

(54) CATHETER HOLE HAVING A FLOW BREAKING FEATURE

(75) Inventors: Austin Jason McKinnon, Herriman, UT (US); Jeff O'Bryan, Murray, UT (US); Chad M. Adams, Cedar Hills, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 77 days.

(21) Appl. No.: 12/853,804

(22) Filed: Aug. 10, 2010

(65) Prior Publication Data

US 2010/0324503 A1    Dec. 23, 2010

Related U.S. Application Data

(63) Continuation-in-part of application No. 12/427,633, filed on Apr. 21, 2009.

(60) Provisional application No. 61/046,843, filed on Apr. 22, 2008.

(51) Int. Cl.
*A61M 5/00* (2006.01)

(52) U.S. Cl.
USPC .......................................................... 604/246

(58) Field of Classification Search
USPC .................. 604/118, 119, 246–256, 523–532
See application file for complete search history.

(56) References Cited

U.S. PATENT DOCUMENTS

| | | |
|---|---|---|
| 3,713,442 A | 1/1973 | Walter |
| 3,828,767 A | 8/1974 | Spiroff |
| 4,292,270 A | 9/1981 | Hannah et al. |
| 4,330,497 A | 5/1982 | Agdanowski |
| 4,563,180 A | 1/1986 | Jervis et al. |
| 4,661,094 A | 4/1987 | Simpson |
| 4,717,381 A | 1/1988 | Papantonakos |
| 4,784,638 A | 11/1988 | Ghajar et al. |
| 4,961,731 A | 10/1990 | Bodicky et al. |
| 4,968,307 A | 11/1990 | Dake et al. |
| 5,037,403 A | 8/1991 | Garcia |

(Continued)

FOREIGN PATENT DOCUMENTS

| | | |
|---|---|---|
| CA | 1323537 C | 10/1993 |
| EP | 0 299 622 A2 | 6/1988 |

(Continued)

OTHER PUBLICATIONS

"AJR: Modified Catheter Can Reduce Contrast Material Injuries," Health Imaging.com, Clinical Studies, http://www.healthimaging.com/index.php?view=article&id=18807%3Aajr-modified-cath . . . , 1 page, Oct. 21, 2009.

*Primary Examiner* — Kevin C Sirmons
*Assistant Examiner* — Imani Hayman
(74) *Attorney, Agent, or Firm* — Jeanne Lukasavage; Craig Metcalf; Kirton McConkie

(57) ABSTRACT

A peripheral catheter having a catheter tip diffuser for reducing an exit velocity of an infusant within the catheter. Pluralities of diffusion side holes are provided on the tip portion of the catheter. Some examples further include pluralities of annularly arranged, staggered diffusion holes provided on the tip portion of an intravenous catheter to streamline infusant issued from the diffusion holes. An inner surface of each diffusion hole is further angled relative to the inner surface of the catheter lumen such that an infusant within the lumen exits the catheter though the diffusion holes at an angle less than 90°.

20 Claims, 17 Drawing Sheets

U.S. PATENT DOCUMENTS

| | | |
|---|---|---|
| 5,085,635 A | 2/1992 | Cragg |
| 5,088,991 A | 2/1992 | Weldon |
| 5,201,723 A | 4/1993 | Quinn |
| 5,234,406 A | 8/1993 | Drasner et al. |
| 5,250,034 A | 10/1993 | Appling et al. |
| 5,267,979 A | 12/1993 | Appling et al. |
| 5,334,154 A | 8/1994 | Samson et al. |
| 5,380,307 A | 1/1995 | Chee et al. |
| 5,536,261 A | 7/1996 | Stevens |
| 5,542,925 A | 8/1996 | Orth |
| 5,578,006 A | 11/1996 | Schön |
| 5,616,137 A | 4/1997 | Lindsay |
| 5,647,846 A | 7/1997 | Berg et al. |
| 5,830,181 A | 11/1998 | Thornton |
| 5,843,017 A | 12/1998 | Yoon |
| 6,052,612 A | 4/2000 | Desai |
| 6,129,700 A | 10/2000 | Fitz |
| 6,132,405 A | 10/2000 | Nilsson et al. |
| 6,293,958 B1 | 9/2001 | Berry et al. |
| 6,514,236 B1 | 2/2003 | Stratienko |
| 6,547,769 B2 | 4/2003 | VanTassel et al. |
| 6,641,564 B1 | 11/2003 | Kraus |
| 6,669,679 B1 * | 12/2003 | Savage et al. ............ 604/500 |
| 6,857,464 B2 | 2/2005 | LeBlanc et al. |
| 6,866,655 B2 | 3/2005 | Hackett |
| 7,108,674 B2 | 9/2006 | Quinn |
| 7,799,014 B2 | 9/2010 | McGuckin, Jr. et al. |
| 2002/0072712 A1 | 6/2002 | Nool et al. |
| 2003/0023200 A1 | 1/2003 | Barbut et al. |
| 2005/0124969 A1 | 6/2005 | Fitzgerald et al. |
| 2005/0197633 A1 * | 9/2005 | Schwartz et al. ............ 604/264 |
| 2006/0027063 A1 | 2/2006 | Currier et al. |
| 2006/0184048 A1 | 8/2006 | Saadat |
| 2007/0073271 A1 | 3/2007 | Brucker et al. |
| 2010/0286657 A1 | 11/2010 | Heck |

FOREIGN PATENT DOCUMENTS

| | | |
|---|---|---|
| EP | 0 947 211 A2 | 10/1999 |
| WO | WO 99/37341 | 7/1999 |
| WO | WO 01/51116 A2 | 7/2001 |
| WO | WO 01/91830 A1 | 12/2001 |
| WO | WO 2009/052506 A1 | 4/2009 |
| WO | WO 2009/132065 A1 | 10/2009 |

* cited by examiner

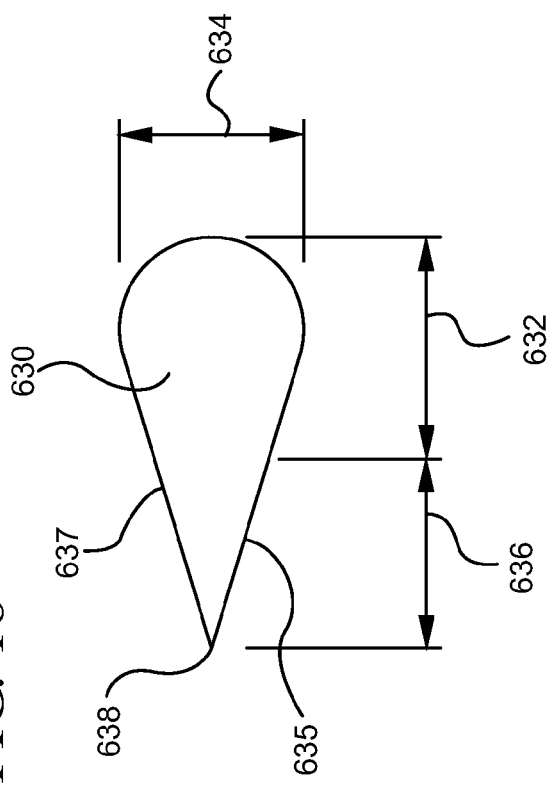
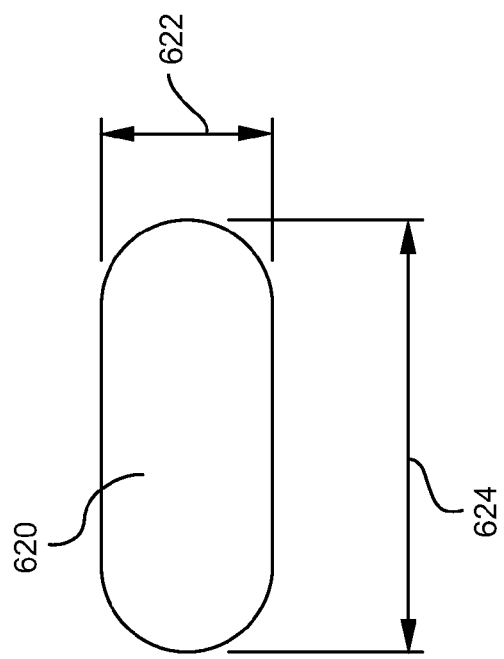
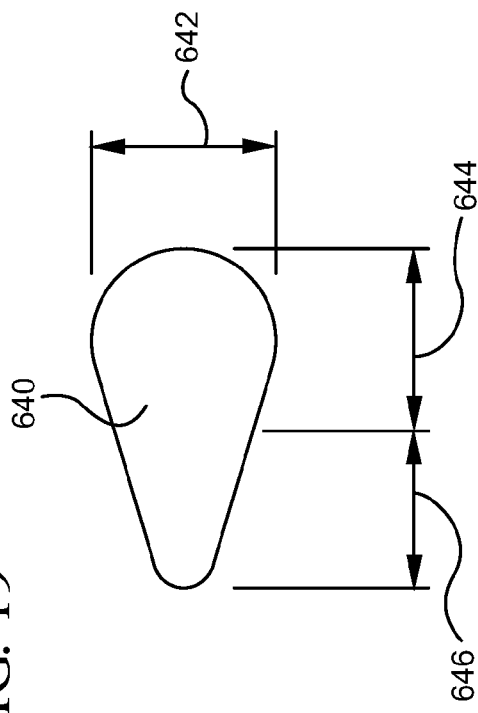

CATHETER HOLE HAVING A FLOW BREAKING FEATURE

RELATED APPLICATIONS

This application is a continuation-in-part of U.S. patent application Ser. No. 12/427,633, filed, Apr. 21, 2009, which claims the benefit of U.S. Provisional Application No. 61/046,843, filed Apr. 22, 2008, entitled POWER PIVC HOLE ARRAY EFFICIENCY IMPROVEMENTS. This application incorporates each by reference and claims priority to both applications.

BACKGROUND OF THE INVENTION

The present invention relates generally to vascular infusion systems and components, including catheter assemblies and devices used with catheter assemblies. In particular, the present invention relates to systems and methods for improving catheter hole array efficiency to provide enhanced infusion flow rates, lower system pressures, and reduced catheter exit jet velocities. Additionally, the present invention relates to improving the energy dissipation of fluid jets issuing from catheter holes.

Vascular access devices are used for communicating fluid with the anatomy of a patient. For example, vascular access devices, such as catheters, are commonly used for infusing fluid, such as saline solution, various medicaments, and/or total parenteral nutrition, into a patient, withdrawing blood from a patient, and/or monitoring various parameters of the patient's vascular system.

A variety of clinical circumstances, including massive trauma, major surgical procedures, massive burns, and certain disease states, such as pancreatitis and diabetic ketoacidosis, can produce profound circulatory volume depletion. This depletion can be caused either from actual blood loss or from internal fluid imbalance. In these clinical settings, it is frequently necessary to infuse blood and/or other fluid rapidly into a patient to avert serious consequences.

Additionally, the ability to inject large quantities of fluid in a rapid manner may be desirable for certain other medical and diagnostic procedures. For example, some diagnostic imaging procedures utilize contrast media enhancement to improve lesion conspicuity in an effort to increase early diagnostic yield. These procedures necessitate viscous contrast media be injected by a specialized "power injector" pump intravenously at very high flow rates, which establishes a contrast bolus or small plug of contrast media in the bloodstream of the patient which results in enhanced image quality.

Power injection procedures generate high pressures within the infusion system, thereby requiring specialized vascular access devices, extension sets, media transfer sets, pump syringes, and bulk or pre-filled contrast media syringes. As the concentration (and thereby viscosity) and infusion rate of the contrast media are increased, bolus density also increases resulting in better image quality via computed tomography (CT) attenuation. Therefore, a current trend in healthcare is to increase the bolus density of the contrast media by increasing both the concentration of the contrast media and the rate at which the media is infused into the patient, all of which ultimately drives system pressure requirements higher.

Intravenous infusion rates may be defined as either routine, generally up to 999 cubic centimeters per hour (cc/hr), or rapid, generally between about 999 cc/hr and 90,000 cc/hr (1.5 liters per minute) or higher. For some diagnostic procedures utilizing viscous contrast media, an injection rate of about 1 to 10 ml/second is needed to ensure sufficient bolus concentration. Power injections of viscous media at this injection rate produce significant back pressure within the infusion system that commonly results in a failure of the infusion system components.

Traditionally, rapid infusion therapy entails the use of an intravenous catheter attached to a peristaltic pump and a fluid source. A patient is infused as a tip portion of the catheter is inserted into the vasculature of a patient and the pump forces a fluid through the catheter and into the patient's vein. Current rapid infusion therapies utilize a catheter and catheter tip with geometries identical to those used with traditional, routine infusion rates. These geometries include a tapering catheter tip such that the fluid is accelerated as the fluid moves through the catheter tip and exits into a patient's vasculature. This acceleration of the infused fluid is undesirable for several reasons.

For example, the tapered catheter results in a greater backpressure for the remainder of the catheter assembly. This effect is undesirable due to the limitations of the pumping capacity of the infusion pump as well as the limited structural integrity of the components and subcomponents of the infusion system. For example, if the backpressure becomes too great, the pump's efficiency may decrease and certain seals or connections within the infusion system may fail. Additionally, the fluid acceleration in the catheter tip results in a recoil force that may cause the catheter tip to shift within the patient's vein thereby displacing the catheter and/or damaging the patient's vein and/or injection site. Fluid acceleration also increases the jet velocity of the infusant at the tip of the catheter. In some procedures, the fluid jet may pierce the patient's vein wall thereby leading to extravasation or infiltration. Not only is this uncomfortable and painful to the patient, but infiltration may also prevent the patient from receiving the needed therapy.

Accordingly, the problem of increased exit velocity of an infusant during rapid infusion procedures remains to be solved. Thus, the present disclosure presents systems and methods to reduce the exit velocity of an infusant while maintaining an increased rate of infusion, as is desirable during rapid infusion procedures. Additionally, the present disclosure presents system modifications for increasing momentum transfer in the jet streams of fluid exiting the catheter.

BRIEF SUMMARY OF THE INVENTION

The systems and methods of the present disclosure have been developed in response to problems and needs in the art that have not yet been fully resolved by currently available infusion systems and methods. Thus, these systems and methods are developed to provide for safer and more efficient rapid infusion procedures.

One aspect of the present invention provides an improved vascular access device for use in combination with a vascular infusion system capable of rapidly delivering an infusant to the vascular system of a patient. The vascular access device generally includes an intravenous catheter configured to access the vascular system of a patient. The intravenous catheter is coupled to the vascular infusion system via a section of intravenous tubing. The material of the intravenous catheter may include a polymer or metallic material compatible with infusion procedures.

In some embodiments, a tip portion of the intravenous catheter is modified to include a plurality of diffusion holes. The tip portion generally comprises a tapered profile, wherein the outer and inner surface of the tip taper towards the distal end of the catheter. The tapered outer surface provides a smooth transition between the narrow diameter of the catheter tip opening and the larger diameter of the catheter tubing. Thus, as the tip of the catheter is introduced into the vein of a patient, the tapered outer surface facilitates easy insertion of the catheter through the access hole. The tapered inner surface is generally provided to tightly contact the outer surface of an introducer needle housed within the lumen of the catheter. The introducer needle is provided to create an opening into the vein of patient through which the catheter tip is inserted. The tapered inner surface ensures a tight seal between the inner surface of the catheter and the outer surface of the needle. Following placement of the catheter, the introducer needle is removed.

As an infusant passes through the tapered portion of the inner surface, the fluid flow of the infusant is accelerated due to the decreased volume through the tapered tip. Thus, in some embodiments a plurality of diffusion holes are formed through the wall thickness of the intravenous catheter so as to provide a plurality of pathways through the wall of the intravenous catheter. Thus, as infusant flows through the catheter toward the tip of the catheter, a portion of the bulk flow through the catheter is diverted through the diffusion holes rather than through the main opening of the catheter tip. As such, the pressure within the infusion system is reduced as compared to systems incorporating standard intravenous catheter. Additionally, the plurality of diffusion holes reduce the jet velocity issued from the tip of the catheter, thereby enabling increased flow rates as required by some diagnostic procedures without additional damage to the vein wall.

In some embodiments, the diffusions holes are arranged on the catheter tip in a staggered array such that an upstream diffusion hole is unaligned with a downstream hole. As such, the fluid flow of an infusant that issues from a downstream diffusion hole is not disturbed by the fluid flow of an infusant that issues from an upstream diffusion hole. This feature provides increased flow efficiency through downstream diffusion holes.

In some embodiments of the present invention, a first set of diffusion holes is disposed in a first annular ring at an upstream, axial position of the catheter tip. A second set of diffusion holes is further disposed in a second annular ring at an axial position of the catheter tip that is downstream from the first annular ring. In some embodiments, the holes of the first annular ring are staggered from the holes of the second annular ring so as to be generally unaligned. In other embodiments, the holes of the first annular ring are axially staggered from the holes of the second annular ring from about 15° to about 60°. Finally, in some embodiments the holes of the first annular ring are axially staggered from the holes of the second annular ring about 45°.

In some embodiments, the diffusion holes are provided through the catheter wall at a predetermined bore angle. Specifically, the diffusion holes of the present invention include an inner wall surface that may be angled relative to the inner surface of the catheter lumen. In some embodiments, the inner surface of a diffusion hole is oriented to an acute angle relative to the inner surface of the catheter lumen. In other embodiments, an inner surface of the diffusion hole is oriented to an angle from about 15° to about 75° relative to the inner surface of the catheter lumen. In some embodiments, the bore angle of the diffusion hole is selected so as to optimize flow efficiency through the diffusion hole, catheter tension within the vein, centralized positioning of the catheter tip within the vein, and reduction of system pressure and tip jet velocity within an infusion system.

In some embodiments, one or more diffusion holes are positioned on the distal end of a catheter body member. Specifically, the diffusion holes include a flow breaking feature. For example, in some embodiments, the flow breaking feature comprises the association of two or more diffusion holes, wherein the axis of each hole is oriented to cross the axis of another hole in the space exterior to the catheter body. As such, the fluid jet streams exiting these holes will collide and disrupt the jet streams. The resulting, scattered jet stream loses energy and momentum more quickly than a singular jet stream, thus decreasing stress and impact on vessel walls.

In some embodiments, the flow breaking feature of the diffusion holes includes a flow disrupter. Specifically, in some embodiments, the flow disrupter includes a wedged extension on the hole. In other embodiments, the flow disrupter includes an inward projection. For example, in some embodiments, the inward projection is disposed on the inner wall surface of the hole. In some embodiments, the hole has a substantially teardrop shape. In some embodiments, the hole has an elongated geometry. The flow disrupter will disrupt the jet stream flowing through the diffusion hole either by breaking it up, or by flattening its shape. Accordingly, a stream exiting the diffusion hole will have a thinner cross section or a disrupted and scattered flow. The resulting, disrupted jet stream loses energy and momentum more quickly than a singular jet stream, thus decreasing stress and impact on vessel walls.

The present invention further includes methods for manufacturing an intravenous catheter for diffusing an infusant. Some methods include the steps of providing an intravenous catheter and forming a plurality of staggered holes through the wall thickness of the intravenous catheter. Some methods of the present invention further include using a laser drill to provide the various staggered holes.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIGS. 12-19 are diffuser hole shapes in accordance with representative embodiments of the present invention.

DETAILED DESCRIPTION OF THE INVENTION

Embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
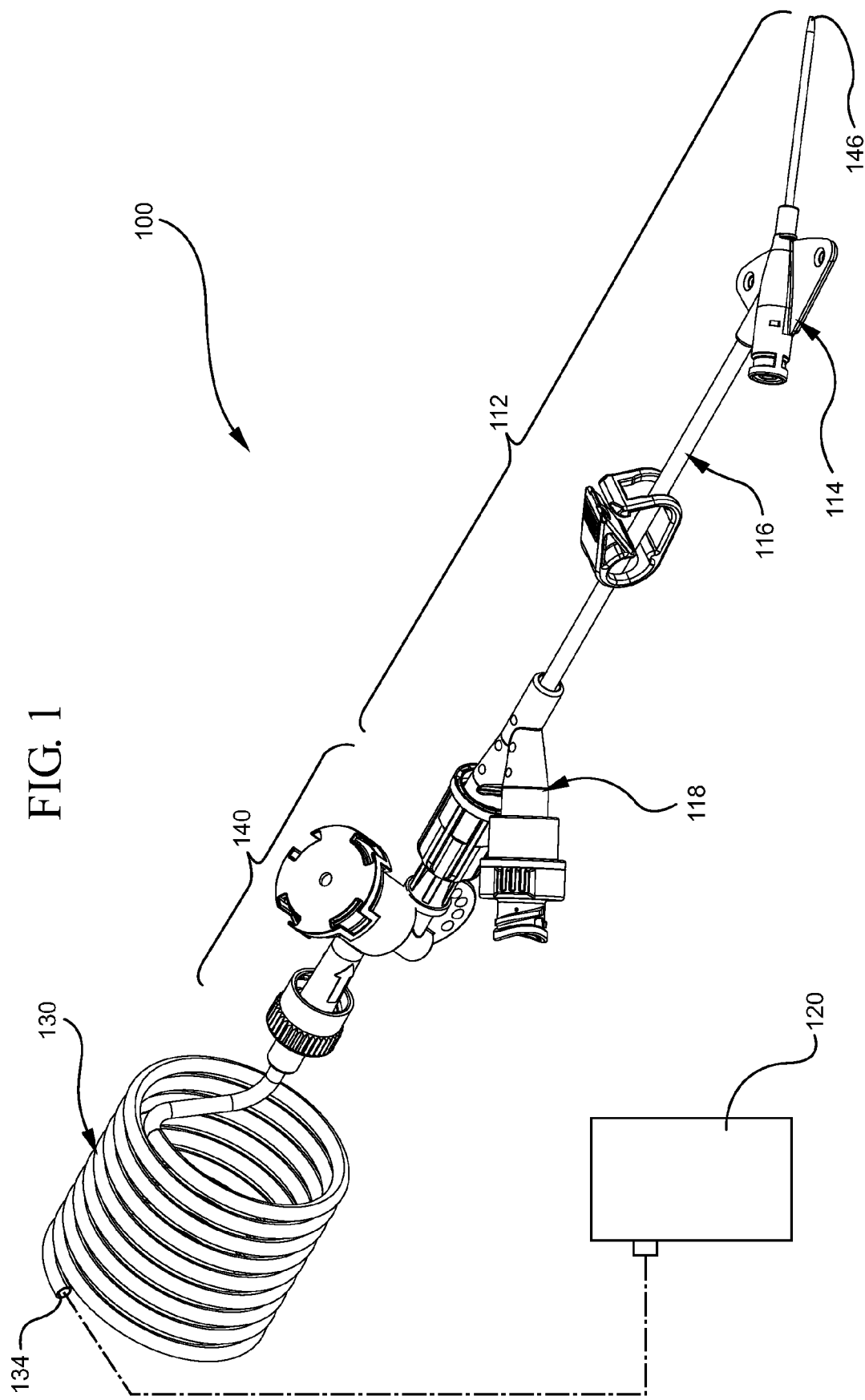
FIG. 1 is a perspective view of an infusion system in accordance with a representative embodiment of the present invention.

The systems and methods of the present invention are generally designed for use in combination with a vascular infusion system capable of rapidly delivering an infusant to the vascular system of a patient. Referring now to FIG. 1, a vascular infusion system 100 is shown, in accordance with a representative embodiment of the present invention. Infusion systems of this type are commonly configured to operate at internal pressures up to 2000 psi. Many systems operate in the range of 75 to 2000 psi, while specific devices of this type operate at 100, 200, and 300 psi. The vascular infusion system 100 comprises a vascular access device 112 coupled to an injector pump 120 via a coiled extension set 130. In some embodiments, the infusion system 100 further comprises a safety device 140 positioned between the vascular access device 112 and the injector pump 120. In some embodiments, a safety device 140 is provided to automatically occlude the fluid path of the infusion system 100, thereby preventing excessive pressure buildup in downstream infusion components.

An injector pump 120 generally comprises a fluid pumping apparatus configured to rapidly deliver an infusant, such as blood, medicaments, and CT scan contrast agents to a patient's vascular system. Desirable infusants may also include various fluids often of high viscosity as required for medical and diagnostic procedures. In some embodiments, the injector pump 120 comprises a power injector capable of delivering an infusant to a patient at flow rates from about 10 mL/hour up to about 1200 mL/minute. In some embodiments, a high infusion flow rate is desirable for medical procedures which require enhanced bolus density of an infusant in a patient's vascular system. For example, a trend in diagnostic imaging procedures is to utilize contrast media enhancement, which requires more viscous contrast media to be pushed into a patient at a higher flow rate, thereby resulting in increased image quality. Thus, in some embodiments an injector pump 120 and a vascular access device 112 are selected to compatibly achieve a desired infusion flow rate.

A coiled extension set 130 generally comprises flexible or semi-flexible polymer tubing configured to deliver an infusant from the injector pump 120 to the vascular access device 112. The extension set 130 includes a first coupler 132 for connecting the extension set 130 to a downstream device 112 or 140. The extension set 130 also includes a second coupler 134 for connecting the extension set 130 to the injector pump 120. A coiled configuration of the extension set 130 generally prevents undesirable kinking or occlusion of the set 130 during infusion procedures. However, one of skill in the art will appreciate that the extension set 130 may include any configuration capable of efficiently delivering an infusant from an injector pump 120 to the patient via a vascular access device 112. In some embodiments, the extension set 130 is coupled between a syringe and a vascular access device whereby an infusant is manually injected into a patient. In other embodiments, the infusion system comprises only a syringe and a vascular access device, in accordance with the present invention.

The vascular access device 112 generally comprises a peripheral intravenous catheter 114. A peripheral intravenous catheter 114 in accordance with the present invention generally comprises a short or truncated catheter (usually 13 mm to 52 mm) that is inserted into a small peripheral vein. Such catheters generally comprise a diameter of approximately a 14 gauge catheter or smaller. Peripheral intravenous catheters 114 are typically designed for temporary placement. The short length of the catheter 114 facilitates convenient placement of the catheter but makes them prone to premature dislodging from the vein due to movement of the patient and/or recoil forces experienced during infusion procedures. Furthermore, unlike midline or central peripheral catheters, peripheral intravenous catheters 114 in accordance with the present invention comprise a tapered catheter tip 146 to accommodate use with an introducer needle (not shown) designed to aid in insertion of the catheter 114.

An introducer needle is typically inserted through the catheter 114 such that a tip of the needle extends beyond the tapered tip 146. The tapered geometry of the tapered tip 146 conforms tightly to the outer surface of the introducer needle. Both the outer surface and the inner surface of the tip 146 are tapered towards the distal end of the catheter 114. The outer surface of the tip 146 is tapered to provide a smooth transition from the smaller profile of the introducer needle to the larger profile of the catheter outer diameter. Insertion of the introducer needle into the vein of the patient provides an opening into the vein through which the tapered tip 146 of the catheter 114 is inserted. The tapered outer surface of the tip 146 enables easy insertion of the catheter 114 into the opening. Once the peripheral intravenous catheter 114 is inserted into the vein of the patient, the introducer needle (not shown) is removed from the lumen of the catheter 114 to permit infusion via the catheter 114.

The tapered inner surface of the tip 146 provides a secure seal between the inner surface of the catheter tip 146 and the outer surface of the introducer needle (not shown). Additionally, the tapered inner surface of the tip 146 causes an acceleration of infusant within the lumen of the catheter as the infusant nears and flows through the catheter tip 146. Specifics regarding the geometries of the tapered inner surface of the tip 146 are provided in connection with FIGS. 3B and 4B below. Following an infusion procedure, the peripheral intravenous catheter 114 is simply removed from vein and discarded.

A desired infusant is typically delivered to the catheter 114 via a section of intravenous tubing 116 coupled to the catheter 114. In some embodiments, a y-adapter 118 is coupled to an end of the tubing 116 opposite the catheter 114, enabling the vascular access device 112 to be coupled to the remainder of the vascular infusion system 100. One of skill in the art will appreciate the possible variations and specific features of available vascular access devices 112, as are commonly used in the medical and research professions. For example, in some embodiments a catheter 114 in accordance with the present invention may include additional access sites, clamps, parallel intravenous lines, valves, couplers, introducer needles, coatings, and/or materials as desired to fit a specific application.

Figure 2:
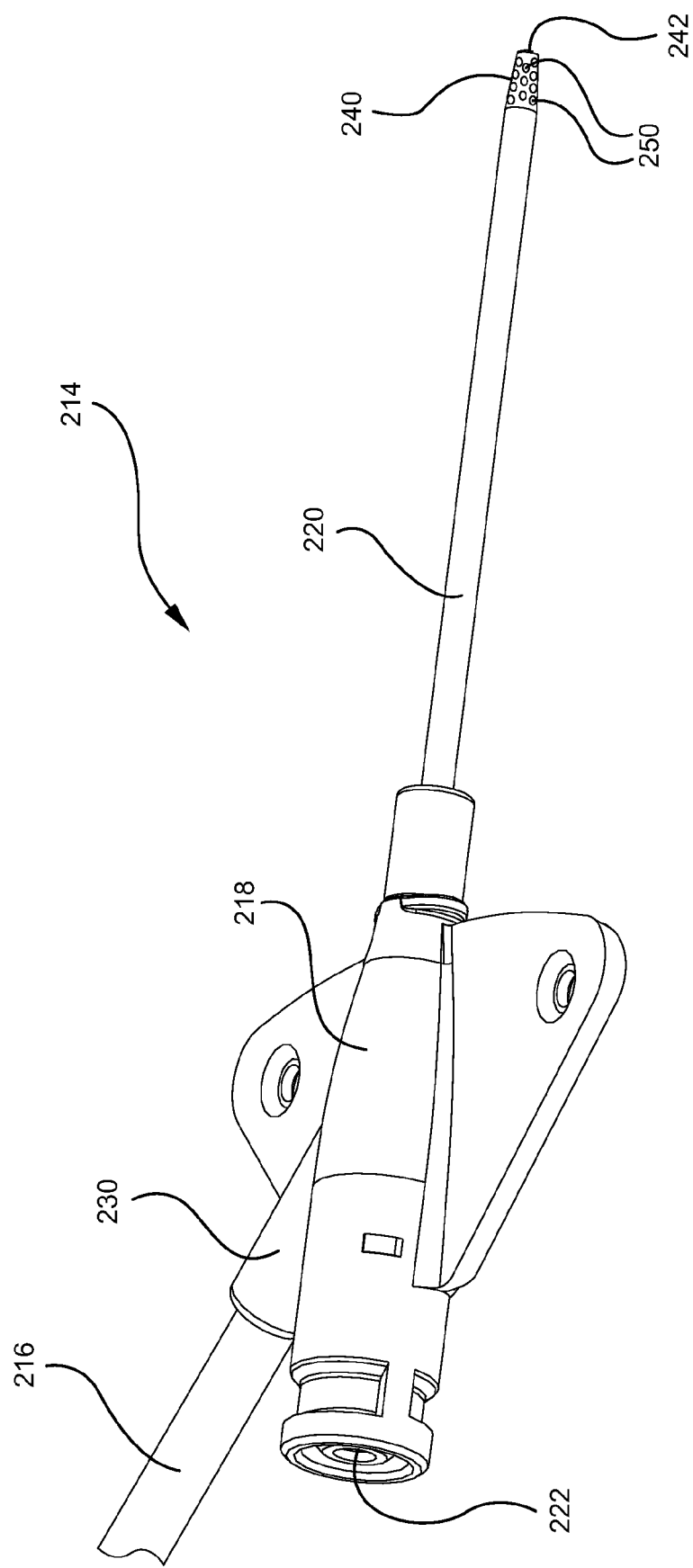
FIG. 2 is a detailed perspective view of a catheter in accordance with a representative embodiment of the present invention.

Referring now to FIG. 2, a catheter 214 is shown in accordance with a representative embodiment of the present invention. Catheter 214 generally comprises a catheter adapter 218 configured to house a tubular body member 220. Catheter adapter 218 further includes an inlet port 230 that is coupled to a section of intravenous tubing 216. The section of intravenous tubing 216 is further coupled to upstream infusion components, as shown and described in connection with FIG. 1, above.

The catheter adapter 218 facilitates delivery of an infusant within the intravenous tubing 216 to a patient via the tubular body member 220. An inner lumen of the catheter adapter 218 is in fluid communication with both an inner lumen of the intravenous tubing 216 and an inner lumen of the tubular body member 220. In some embodiments, catheter adapter 218 further comprises an access port 222. The access port 222 is generally provided to permit direct access to the inner lumen of the catheter adapter 218. In some embodiments, the access port 222 is accessed via a needle and a syringe to deliver an infusant to a patient via the tubular body member 220. In other embodiments, an introducer needle or guide wire is inserted into the access port 222 and advanced through the inner lumen of the tubular body member 220. In some embodiments, a tip portion of the introducer needle or guide wire (not shown) extends beyond a tip portion 240 of the tubular body member 220. As such, the tip portion of the introducer needle or guide wire may provide an opening into the vascular system of a patient into which the tubular body member 220 is inserted. Following placement of the tubular body member 220 into the vein of the patient, the introducer needle or guide wire is removed from the access port 222 thereby establishing fluid communication between the tubular body member 220, the catheter adapter 218 and the intravenous tubing 216.

In some embodiments, the tubular body member 220 comprises an intravenous catheter. The intravenous catheter 220 generally comprises a flexible or semi-flexible biocompatible material, as commonly used in the art. In some embodiments, the intravenous catheter 220 comprises a polymer material, such as polypropylene, polystyrene, polyvinylchloride, polytetrafluoroethylene, and the like. In other embodiments, the intravenous catheter 220 comprises a metallic material, such as surgical steel, titanium, cobalt steel, and the like.

The tubular body member 220 may comprise any length, where the length is selected based on the intended application of the catheter 214. For some applications, the tubular body member 220 is inserted into a peripheral vein of the patient. In other applications, the tubular body member 220 is inserted into a central vein of the patient. For rapid infusion applications, the tip portion 240 of the tubular body member 220 is modified to include a plurality of diffusion holes 250. The diffusion holes 250 are generally provided to divert fluid from the main channel of flow through the inner lumen of the tubular body member 220. As such, the diffusion holes 250 effectually slow the jet of infusant which issues from the catheter tip 240 during rapid infusion procedures. Additionally, the plurality of diffusion holes 250 increase the accumulative area of the catheter tip opening 242 to relieve the overall pressure in the vascular infusion system 100.

Figure 3A:
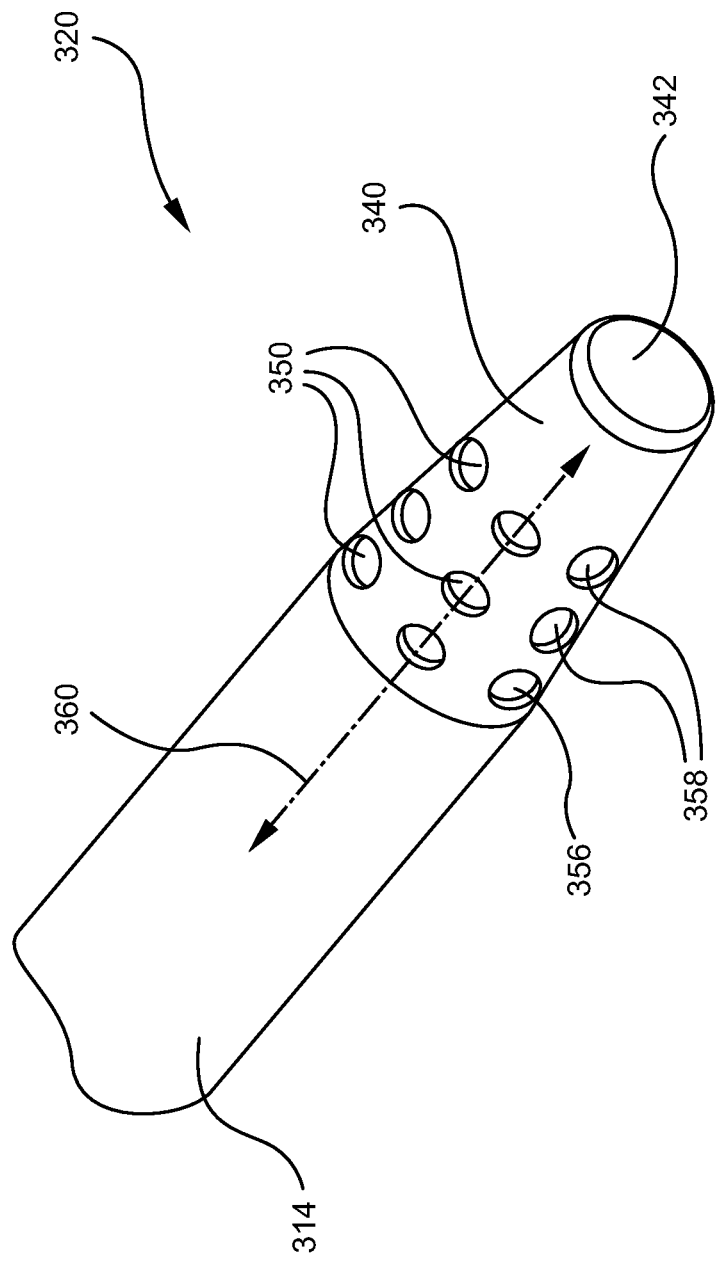
FIG. 3A is a perspective view of a catheter tip in accordance with a representative embodiment of the present invention.

Referring now to FIG. 3A, a distal end portion 320 of an intravenous catheter 314 is shown, in accordance with a representative embodiment of the present invention. As previously discussed, an external surface of the tip 340 is tapered so as to provide a gradual transition from the catheter opening 342 of the tip 340 to the diameter of the catheter body 314. In some embodiments, the tip 340 of the intravenous catheter 314 is modified to include a plurality of side holes 350. The side holes 350 are generally positioned on the tapered tip 340 of the catheter 314 to provide an access through which infusant within the catheter 314 may issue. The surface area of the side holes 350 combine with the surface area of the lumen opening 342 to increase the overall surface area through which an infusant may issue from the tip 340 of the intravenous catheter 314. The side holes 350 are annularly organized on the tip 340 of the intravenous catheter 314 so as to align adjacent holes along a common axis 360. As such, an upstream hole 356 is directly aligned with downstream holes 358.

Figure 3B:
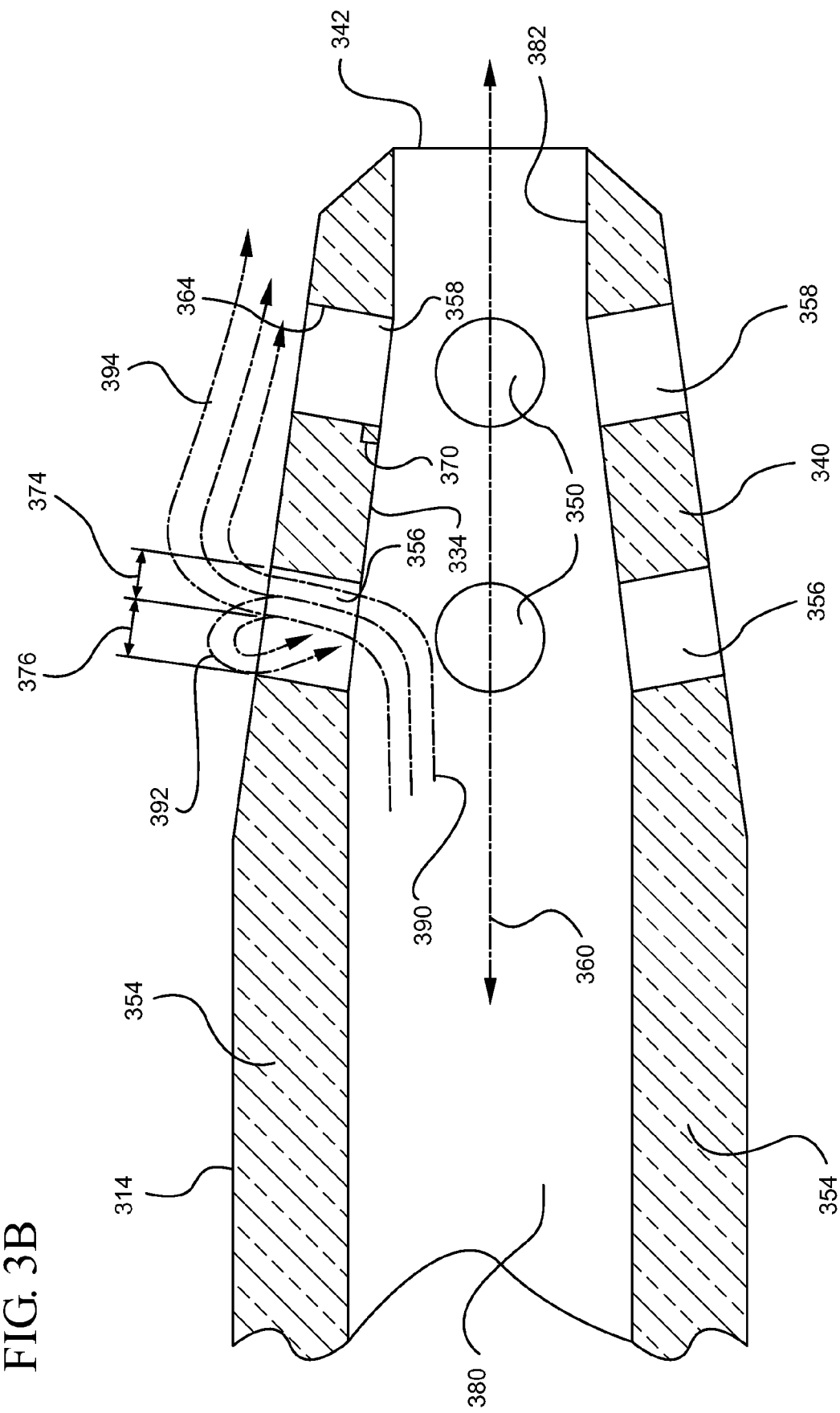
FIG. 3B is a cross-section side view of the catheter tip of FIG. 3A in accordance with a representative embodiment of the present invention.

Referring now to FIG. 3B, a cross-sectioned view of the intravenous catheter 314 of FIG. 3A is shown. As previously discussed, a portion 334 of the internal surface of the tip 340 is tapered which causes an acceleration in the fluid flow 390 through the tip 340. The side holes 350 of the intravenous catheter 314 are formed through the catheter wall 354 such that an inner surface 364 of each hole 350 is oriented at an angle 370 of approximately 90° relative to an inner surface 382 of the catheter lumen 380. The side holes 350 are generally positioned within the tapered portion 334 of the tip 340 such that as the velocity of the fluid flow 390 increases through the tapered portion 334, infusant 394 is permitted to issue through the side holes 350. As infusant issues through the side holes 350, fluid pressure within the lumen 380 is decreased. Additionally, as infusant issues through the side holes 350, tip jet velocity of the infusant also decreases.

Computational fluid dynamic analysis of the 90° side holes 350 reveals that only a first half 374 of each hole 350 cross section is utilized by the fluid flow 390. In some embodiments, a second half 376 of the 90° side holes 350 cross section comprises a recirculation eddy 392. Therefore, in some embodiments the 90° side hole 350 configuration may demonstrate approximately fifty percent flow efficiency through each side hole 350.

Figure 4A:
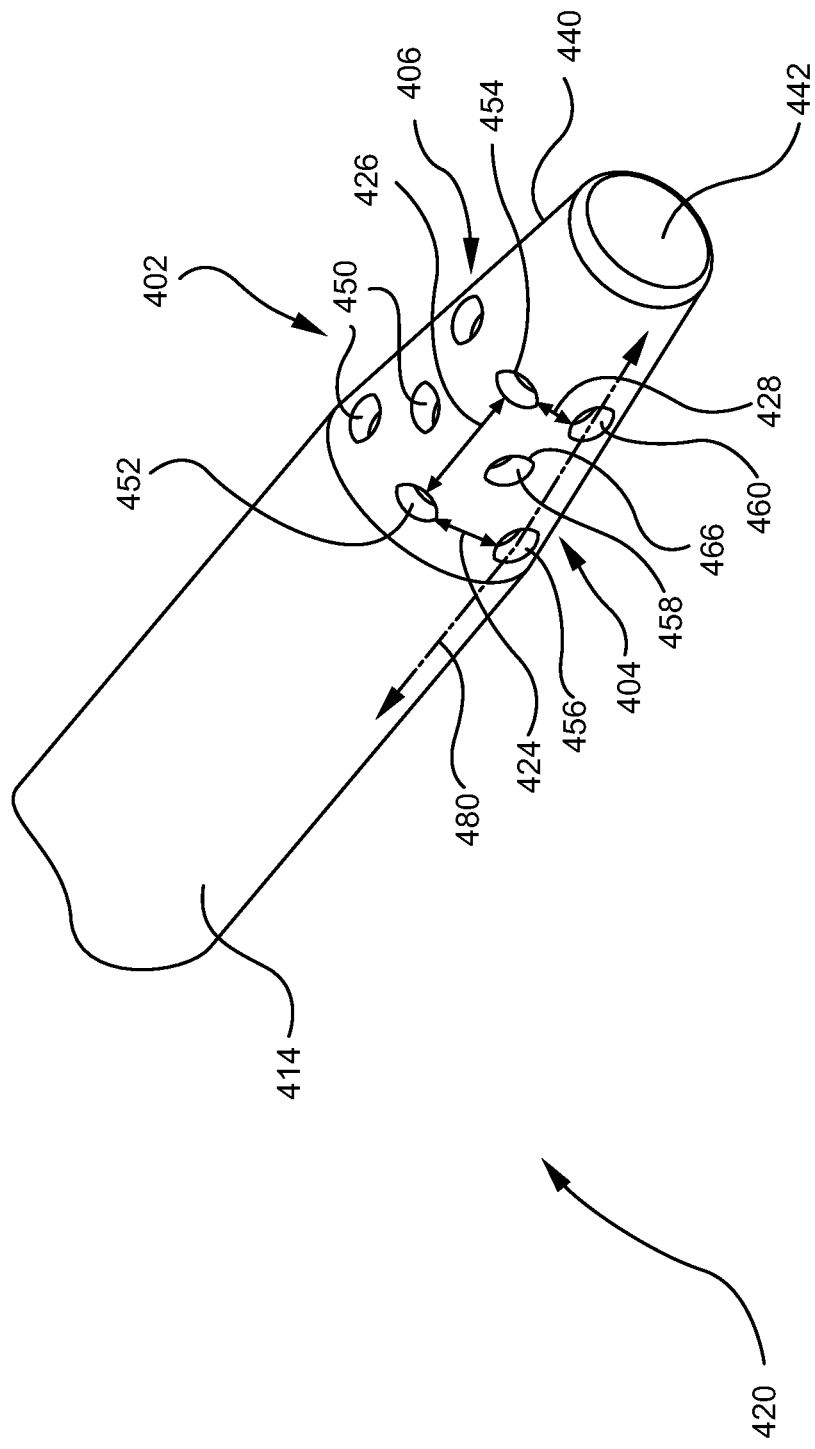
FIG. 4A is a perspective view of a catheter tip in accordance with a representative embodiment of the present invention.

Referring now to FIG. 4A, a distal end portion 420 of an intravenous catheter 414 is shown in accordance with a representative embodiment of the present invention. The intravenous catheter 414 has been modified to include a plurality of staggered diffusion holes 450. One having skill in the art will appreciate that the number and dimensions of the diffusion holes 350 and 450 may be varied and adjusted to achieve a desired flow rate, a reduction in tip jet velocity, a reduction in vascular damage, and increased bolus density. Diffusion holes 350 and 450 are generally provided by manufacturing methods known in the art. For example, in some embodiments the plurality of diffusion holes 350 and 450 are provided with a laser drill.

In some embodiments, a selected array of the diffusion holes 450 increases the distance between adjacent holes 450 thereby structurally strengthening the tip 440 of the intravenous catheter 414, as compared to some linear hole arrays. In other embodiments, a selected array of the diffusion holes 450 further streamlines infusant issued from the diffusion holes 450 thereby reducing the energy necessary to divert bulk flow from the main stream of the catheter lumen 490 into the diffusion holes 450.

For example, in some embodiments of the present invention the diffusion holes 450 have been arranged in a staggered configuration, as shown. Accordingly, an upstream hole 456 is unaligned with an adjacent, downstream hole 458. Furthermore, downstream hole 458 is unaligned with an adjacent, downstream hole 460. In some embodiments, upstream hole 456 is directly aligned with downstream hole 460 along a common axis 480. In other embodiments, upstream hole 456, downstream hole 458 and downstream hole 460 are each unaligned with each other, such that none of the holes are aligned along a common axis. In some embodiments, an upstream hole 456 is axially staggered from a downstream hole 458 from about 15° to about 60°. Finally, in some embodiments, an upstream hole 456 is axially staggered from a downstream hole 458 approximately 45°.

The diffusion holes 450 are annularly organized on the tapered portion of the tip 440 of the intravenous catheter 414 in a staggered configuration, as previously discussed. A first annular ring 402 comprises a plurality of diffusion holes 450 forming a first upstream ring of diffusion holes. In some embodiments, the holes of the first annular ring 402 are axially spaced an equal distance from adjacent holes of the first annular ring 402. In other embodiments, a non-uniform axially spacing is applied to the holes of the first annular ring 402. In some embodiments, a second annular ring 404 is provided downstream from the first annular ring 402, the diffusion holes of the second annular ring 404 being staggeredly positioned relative to the diffusion holes of the first annular ring 402. Finally, in some embodiments a third annular ring 406 is provided downstream from the second annular ring 404, the diffusion holes of the third annular ring 406 being staggeredly positioned relative to the diffusion holes of the second annular ring 404.

A gap 424 is provided between adjacent holes of the first annular ring 402. In some embodiments, the gap 424 is provided to accommodate the width of downstream hole 458, such that the downstream hole 458 and the gap 424 are aligned along a common axis (not shown). Furthermore, a downstream gap 428 is provided to accommodate the width of an upstream hole 466, such that the upstream hole 466 and the downstream gap 428 are aligned along a common axis (not shown). The axial alignment of the upstream gap 424 and the downstream hole 458 prevents wake effect due to the absence of a diffusion hole directly upstream from the downstream hole 458. Similarly, the axial alignment of the downstream gap 428 and the upstream hole 466 prevents wake effect due to the absence of a diffusion hole directly downstream from the upstream hole 466.

The staggered configuration of the first, second and third annular rings 402, 404 and 406 provides an elongate gap 426 forming a space between an upstream diffusion hole 452 of the first annular ring and an axially aligned downstream diffusion hole 454 of the third annular ring 406. The length of the elongate gap 426 generally provides sufficient distance between an upstream diffusion hole 452 and a downstream diffusion hole 454, so that the fluid pressure of an infusant from the upstream hole 452 is approximately equal to the fluid pressure of an infusant from the downstream hole 454. Thus, the staggered configuration of the diffusion holes 450 ensures equal flow efficiency from upstream and downstream diffusion holes 452 and 454.

Figure 4B:
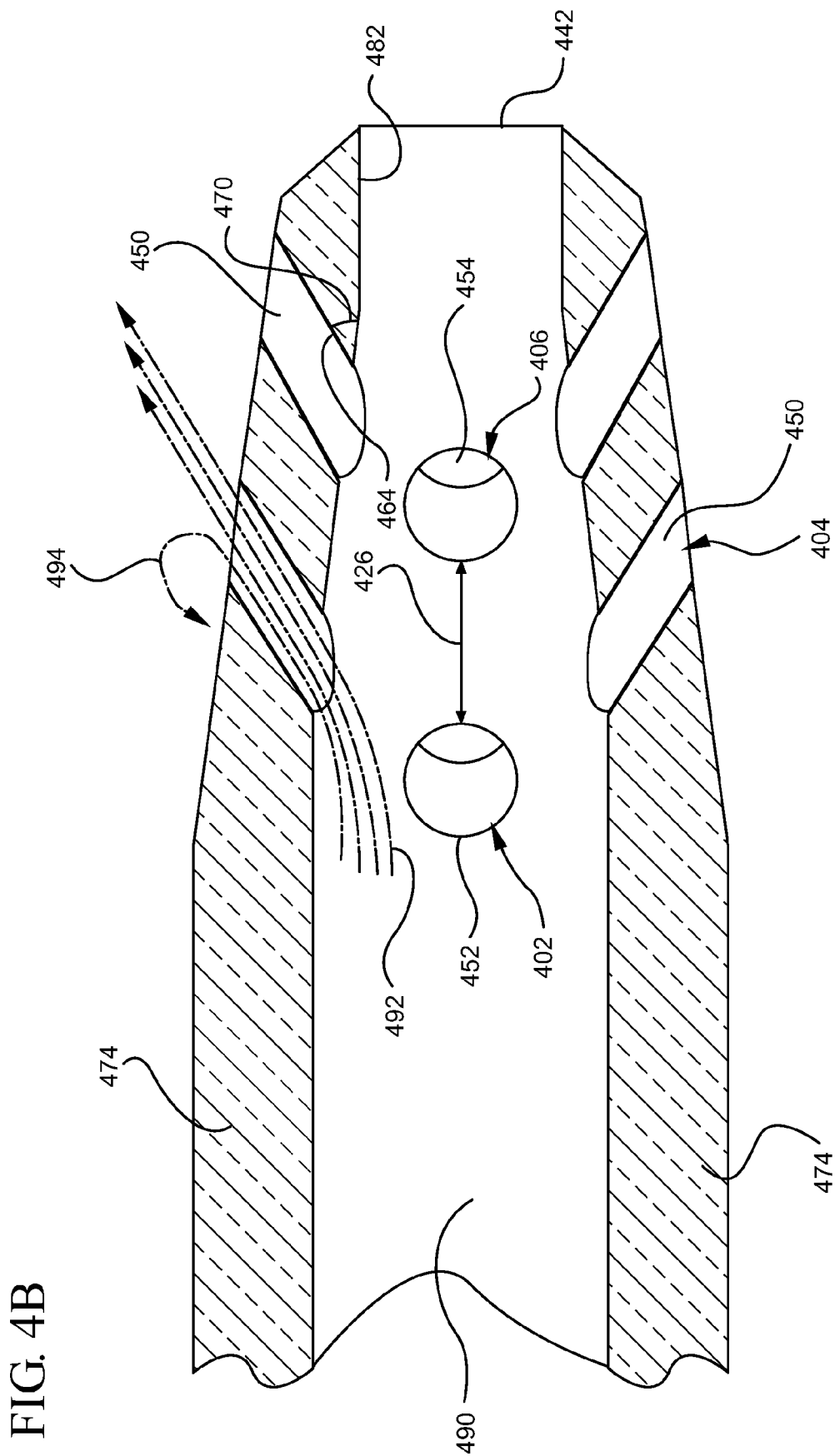
FIG. 4B is a cross-section side view of a catheter tip in accordance with a representative embodiment of the present invention.

In some embodiments, the diffusion holes 450 are formed through the catheter wall 474 such that an inner surface 464 of each hole 450 is oriented at an angle 470 that is acute to an inner, tapered surface 482 of the catheter lumen 490, as shown in FIG. 4B. In some embodiments, the angle 470 is between about 15° to about 75°. In other embodiments, the angle 470 is approximately 45°.

Figure 7A:
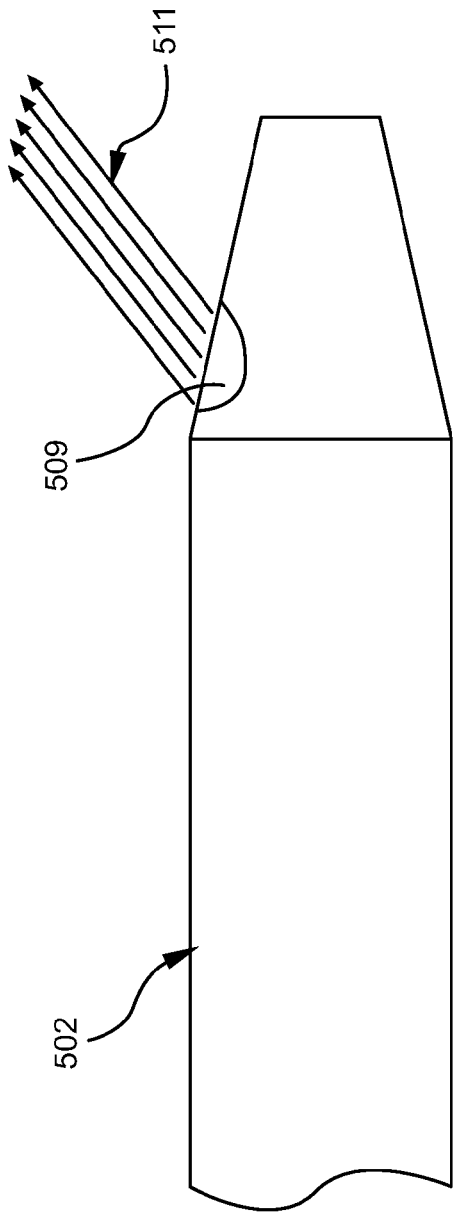
FIG. 7A is a perspective view of a catheter tip in accordance with a representative embodiment of the present invention.
Figure 7B:
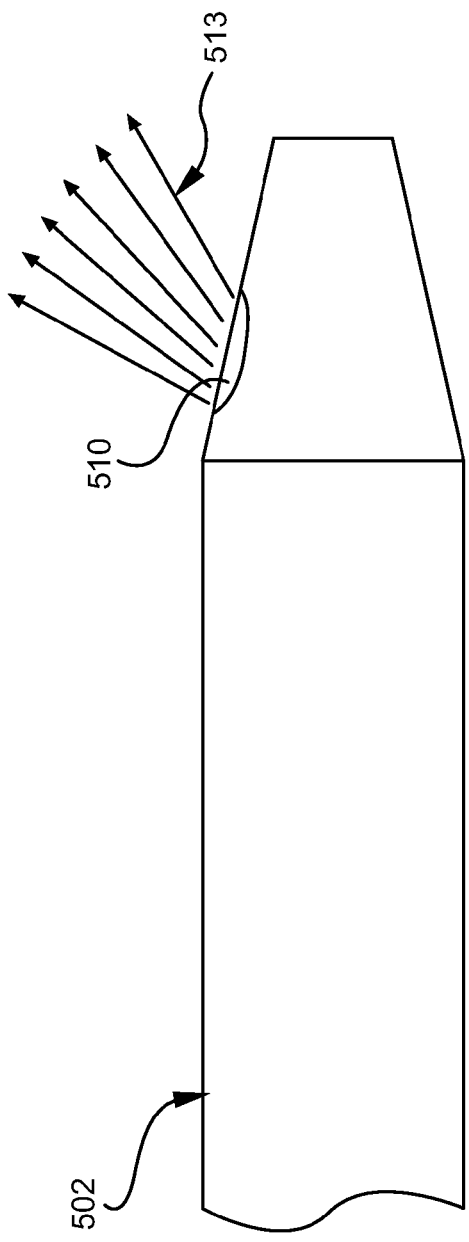
FIG. 7B is a perspective view of a catheter tip in accordance with a representative embodiment of the present invention.

As hereinbefore set forth, diffusion holes and diffusion hole arrays diminish the exit force of fluid issuing from a catheter tip. Attention will now be drawn to the geometry of the diffusion holes (also referred to herein simply as "holes"), and specifically to geometries which further diminish the exit force of fluid issuing from a catheter tip. FIGS. 2-4B generally depict circular diffusion holes. However, in some embodiments, one or more diffusion hole may be non-circular. As illustrated in FIG. 7A, a circular hole 509 of a catheter 502 issues a substantially cylindrical jet of fluid 511 into the vasculature of a patient. In general, this jet 511 is concentrated and direct and breaks up slowly within the vein. It follows that a non-circular hole 510, as illustrated in FIG. 7B, issues a jet of fluid 513 having a substantially non-circular cross section, and thus greater surface area. The increase in surface area of the jet 513 increases the rate of momentum transfer between the jet 513 and the intravenous environment compared to that of more cylindrical jet 511 of FIG. 7A. Thus, the jet 513 issuing from the non-circular hole 510 disperses and decelerates more quickly, posing less of a threat of extravascation to vein walls.

Figure 20:
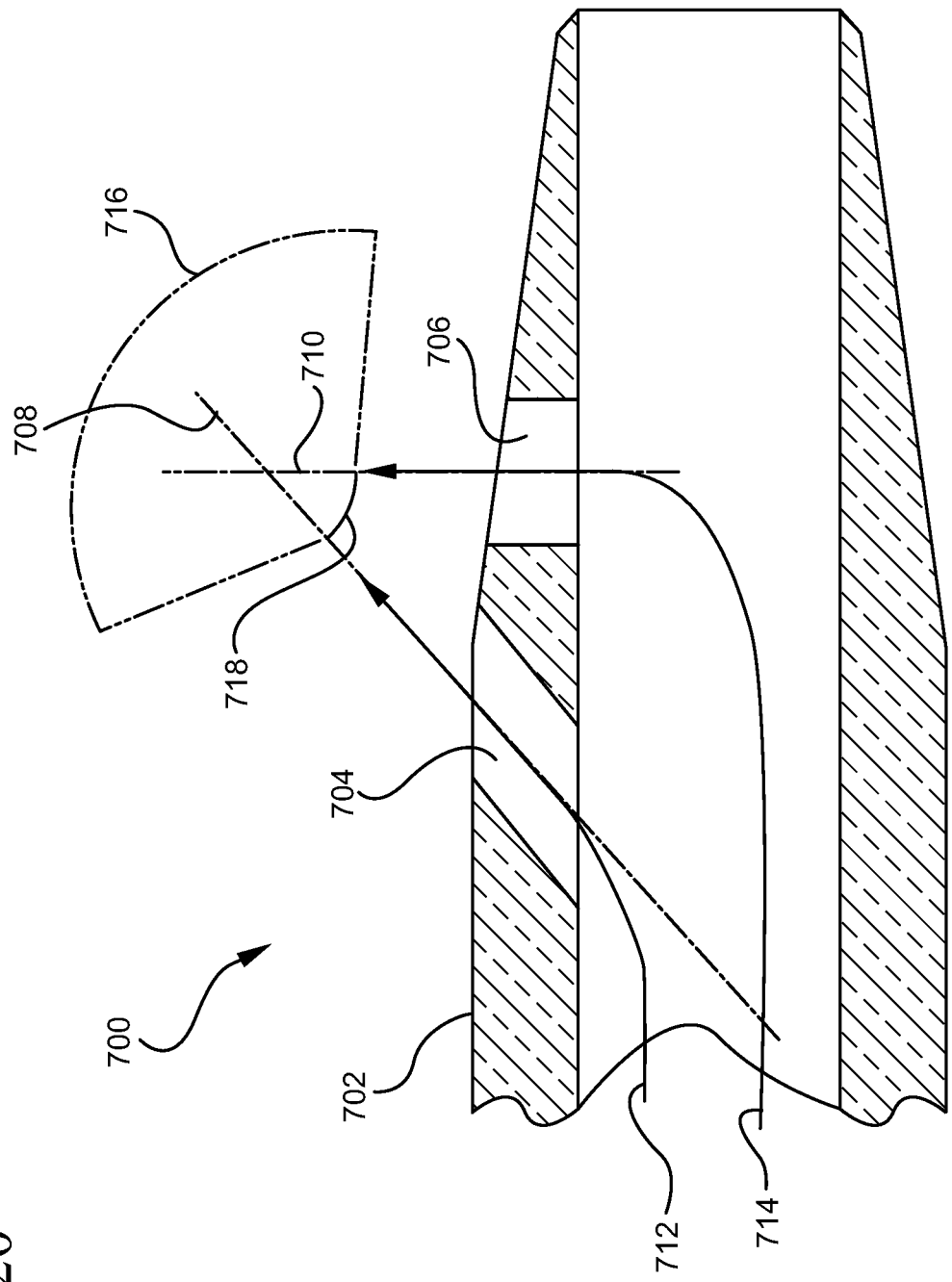
FIG. 20 is a cross-section side view of a catheter tip in accordance with a representative embodiment of the present invention.
Figure 21:
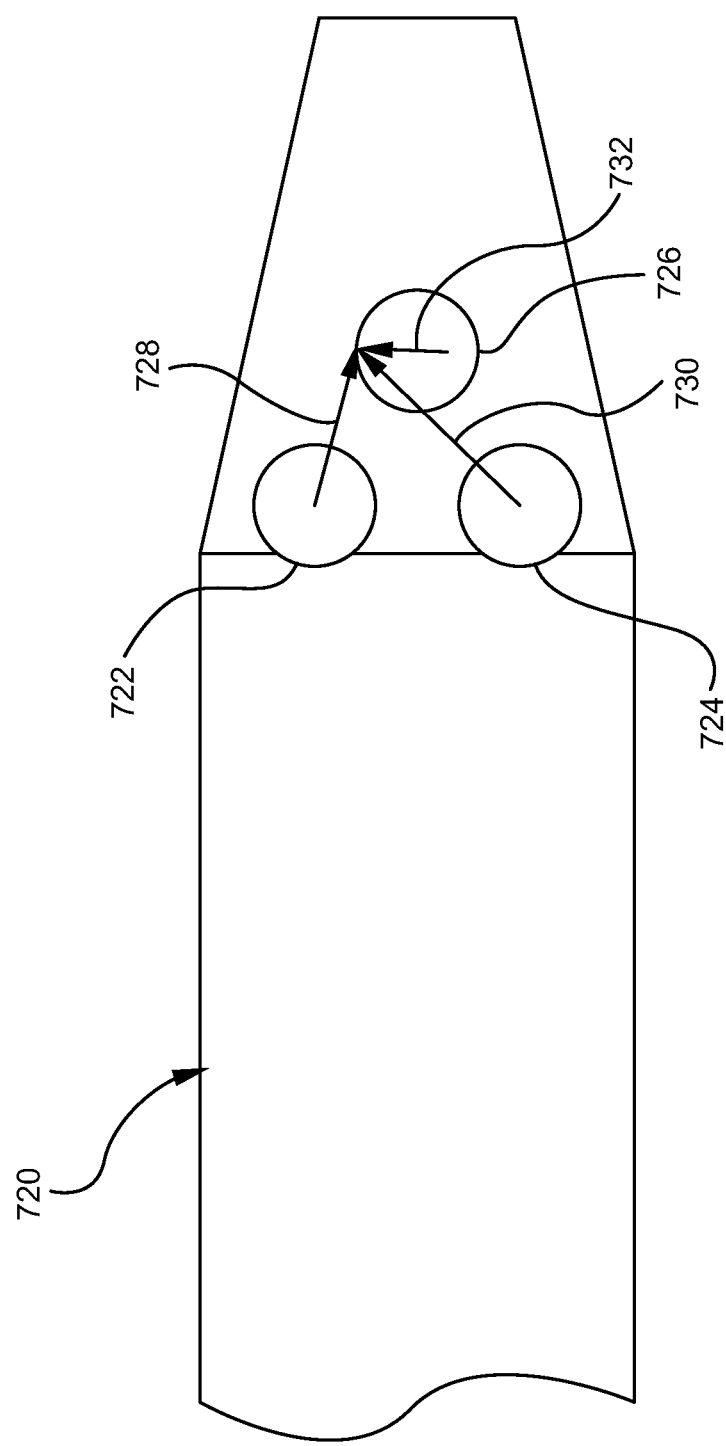
FIG. 21 is a perspective view of a catheter tip in accordance with a representative embodiment of the present invention.

In addition to employing non-circular hole geometries, flow disruption may also be facilitated by including additional flow breaking feature on the diffusion hole. A "flow breaking feature" refers to a feature of the hole that substantially breaks up, thins, or slows a jet of fluid exiting a hole so that the jet will lose speed more quickly within the vein. Flow breaking features are hole features that facilitate the break up the flow of a fluid jet as it passes through and/or exits the hole. Flow breaking features include a flow disrupter, elongated hole geometries, and hole orientations such that the axis of flow of two or more holes collides. Non-limiting examples of a hole breaking features including two or more holes whose axis of flow collide are illustrated in FIGS. 20-21.

As indicated, one type of flow breaking features is a flow disrupter. A "flow disrupter" refers to a deviation in a hole's geometry from a rounded hole, a circular hole, or an elliptical hole. Thus, flow disrupters include inward projections and pointed extensions. A non-limiting example of a hole having a flow disrupter is a substantially tear-shaped hole including a pointed extension. Another non-limiting example of a hole having a flow disrupter is a hole having one or more inward projection. An "inward projection" refers to a portion of a hole's periphery which projects toward the inner portion of the hole. In this way, there exists a cross sectional area of the hole in which a straight line interposed over the cross section could cross the perimeter of the hole more than two times, as illustrated in FIG. 12. Non-limiting examples of such inward projections are illustrated in FIGS. 8-16.

Figure 8:
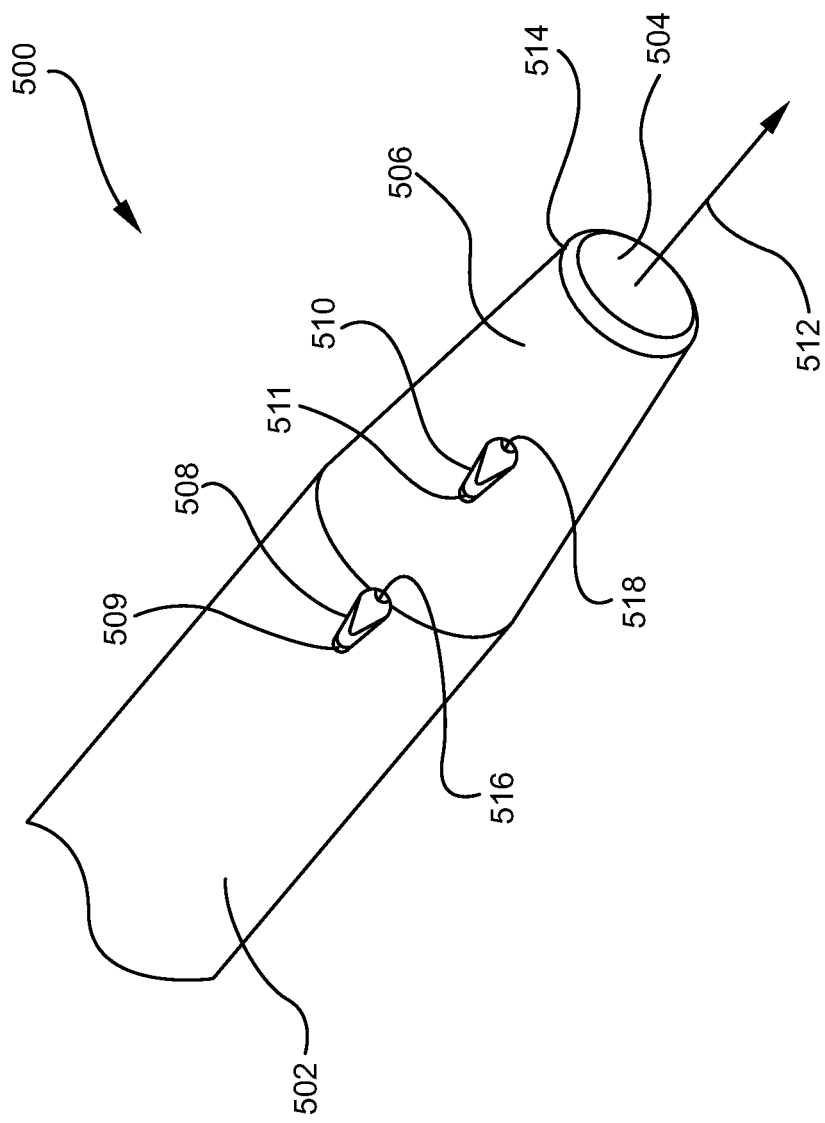
FIG. 8 is a perspective view of a catheter tip in accordance with a representative embodiment of the present invention.
Figure 9:
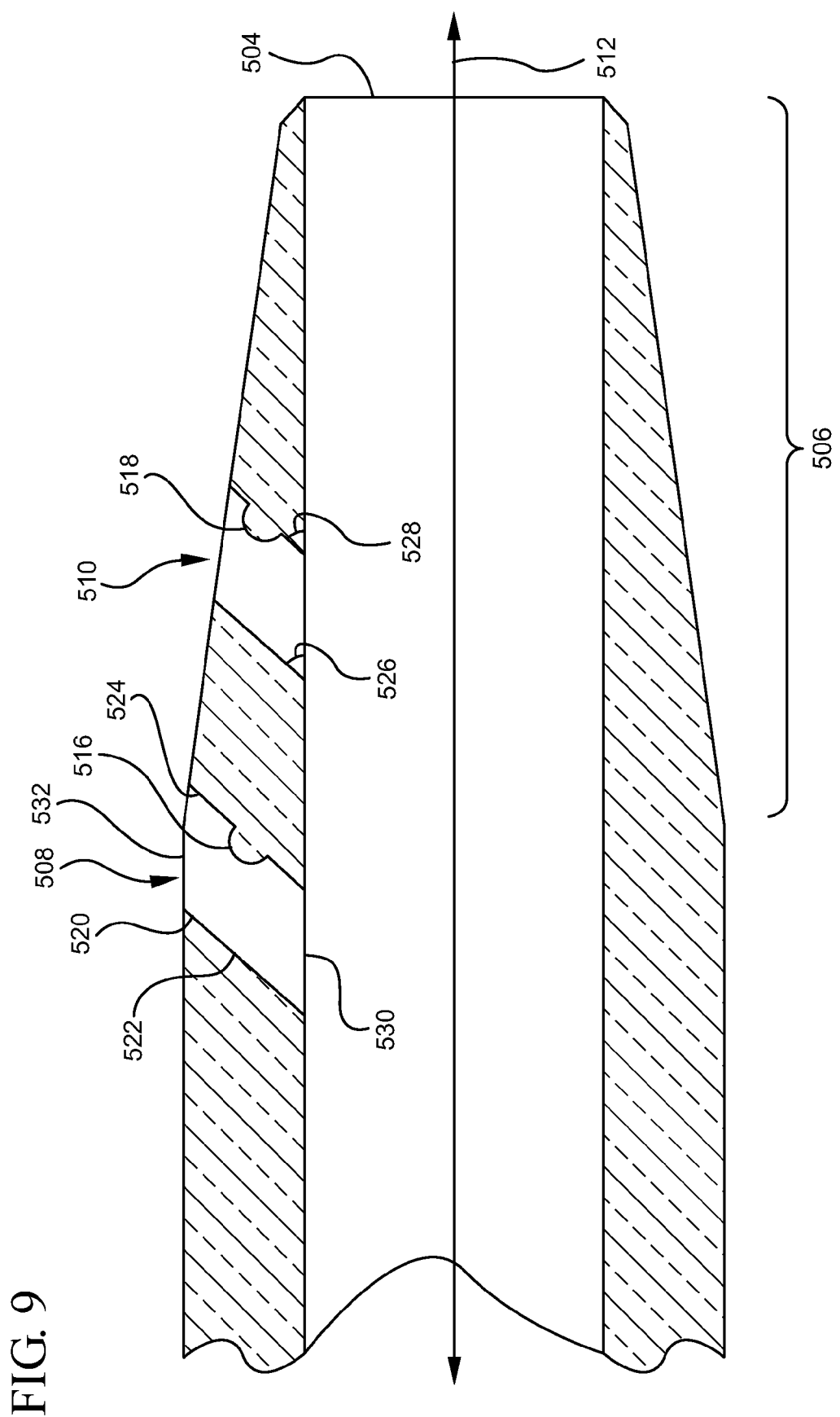
FIG. 9 is a cross-section side view of the catheter tip of FIG. 8.

Referring now to FIGS. 8-9, a distal end portion 514 of an intravenous catheter 502 is shown in accordance with a representative embodiment of the present invention. The intravenous catheter 502 has been modified to include a plurality of non-circular diffusion holes 508 and 510 in addition to the distal lumen opening 504. The number and dimensions of the diffusion holes 508 and 510 may be varied and adjusted to achieve a desired flow rate, a reduction in tip jet velocity, a reduction in vascular damage, and increased bolus density. As illustrated, at least a portion of each diffusion hole is located on the tapered portion 506 of the catheter tip such that all fluid is introduced into the patient near the catheter tip. In other embodiments a diffusion hole is entirely disposed outside of the tapered portion of catheter tip but near the distal portion 514 of the catheter 502.

Referring now to FIG. 9, a cross-sectional view of the catheter 502 is illustrated taken along the center of the diffusion holes 508 and 510. As illustrated, the holes 508 and 510 are oriented at an angle 528 with respect to the center axis 512 of the catheter lumen. In some embodiments, the angle 528 between the center axis 512 of the catheter lumen and the distal surface of the hole 524 (the "distal hole angle") is the same as the angle 526 between the center axis 512 of the catheter lumen and distal surface of the hole 524 (the "proximal hole angle"). In other embodiments, the distal hole angle 528 and the proximal hole 526 angle differ in order to provide a more diffused jet of fluid from the hole. For example, if the distal hole angle 528 is greater than the proximal hole angle 526, fluid flows within the hole collide, disrupting the exiting jet, and increasing the energy dissipation of the resulting jet. In other embodiments, the distal hole angle 528 is less than the proximal hole angle 526 so that a jet of fluid exiting the hole expands and disperses as it passes through the hole.

Fluid passing through the catheter 508 travels generally down the lumen toward the catheter lumen opening 504. The inner surface of the lumen includes one or more inner hole openings 530, through which some fluid enters. As fluid travels through the hole, structures and geometries of the inner wall surface 520 of the hole modify the jet of fluid that exits through the outer hole opening 532. Additionally, the shapes of the inner and outer hole openings 530 and 532 affect the exiting jet of fluid. In some embodiments, the shape of the inner hole opening differs from the shape of the outer hole opening to modify the exiting fluid stream with enhanced dissipation properties.

With continued reference to FIGS. 8-9, fluid flow exiting the diffusion holes 508 and 510 is disrupted by two flow disrupters associated with each diffusion hole. Specifically, holes 508 and 510 include a tear-drop shape, or tear-drop shaped cross section, having a pointed extension 509 and 511. The pointed extension increases the surface area of the issuing jet to improve flow break up. The holes 508 and 510 additionally comprise an inward projection 516 and 518 disposed on the inner wall surface of the diffuser hole. The inward projection extends inward toward an inner portion of the hole. As fluid rapidly flows through the hole, the inward projection disrupts the direct flow, creating turbulence within jet issuing from the hole. Turbulence within the jet can cause jet break up, jet expansion, jet slowing, and ultimately increase will increase rate at which momentum that is transferred from the jet to the intravenous environment.

Figure 10A:
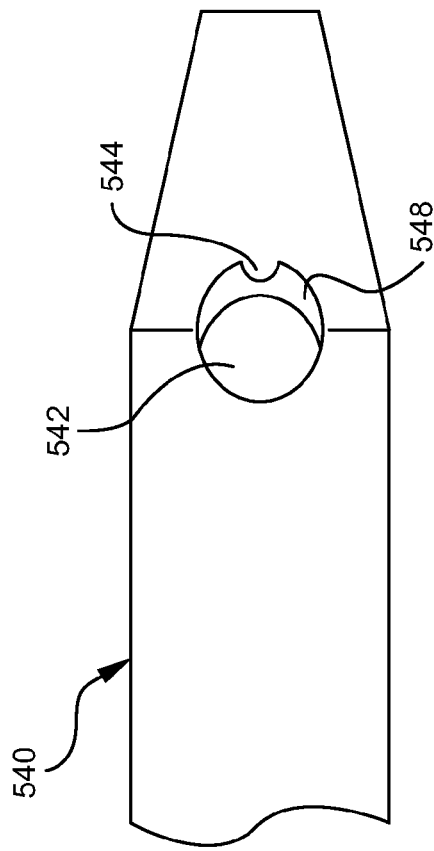
FIG. 10A is a perspective view of a catheter tip in accordance with a representative embodiment of the present invention.
Figure 10B:
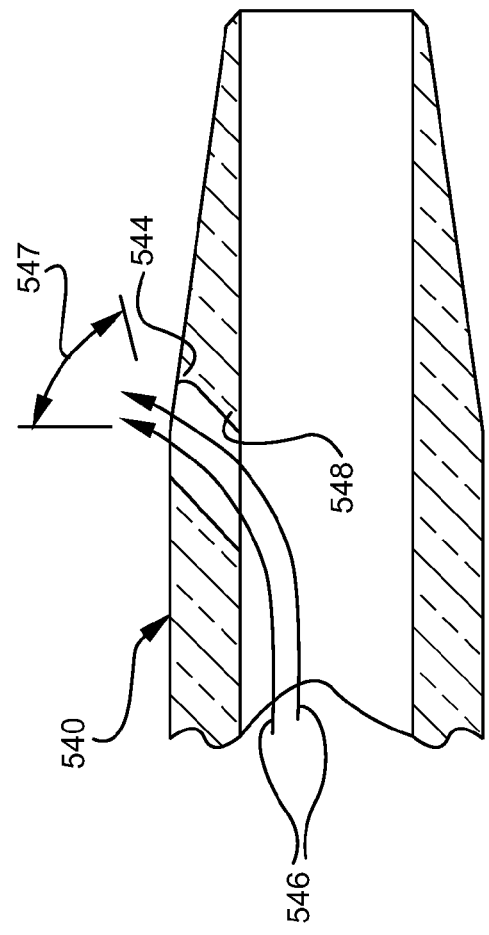
FIG. 10B is a cross-section side view of the catheter tip of FIG. 10A.

FIGS. 10A-16 illustrate additional embodiments of inward projections which cause breakup within a fluid jet exiting a diffusion hole. Referring now to FIG. 10A-10B, a diffuser hole 542 in a catheter 540 includes an inward projection 544. The inward projection is disposed on the inner wall surface 548 of the hole 542 near the hole exit. In this way, the flow of fluid passing through the hole 542 is disrupted by the inward projection that forces fluid flow paths 546 within the hole 542 to collide with one another, create turbulence, and thus create increased dispersion and an expanded jet trajectory 547 of the exiting fluid jet.

Figure 11A:
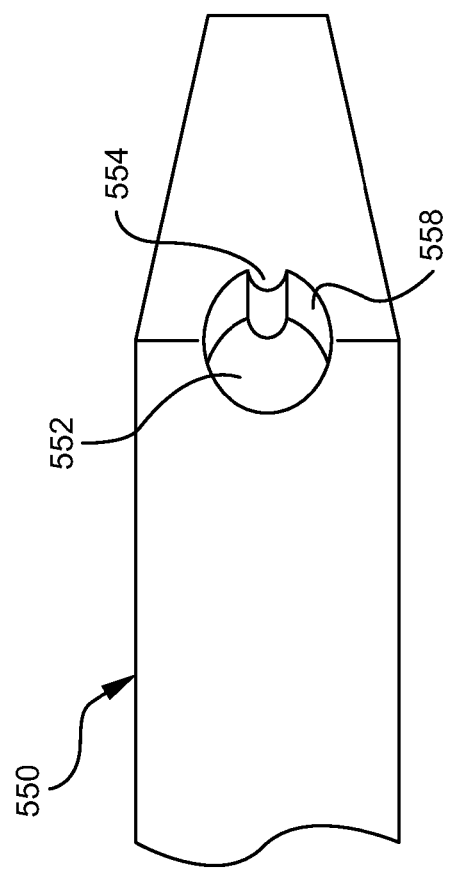
FIG. 11A is a perspective view of a catheter tip in accordance with a representative embodiment of the present invention.
Figure 11B:
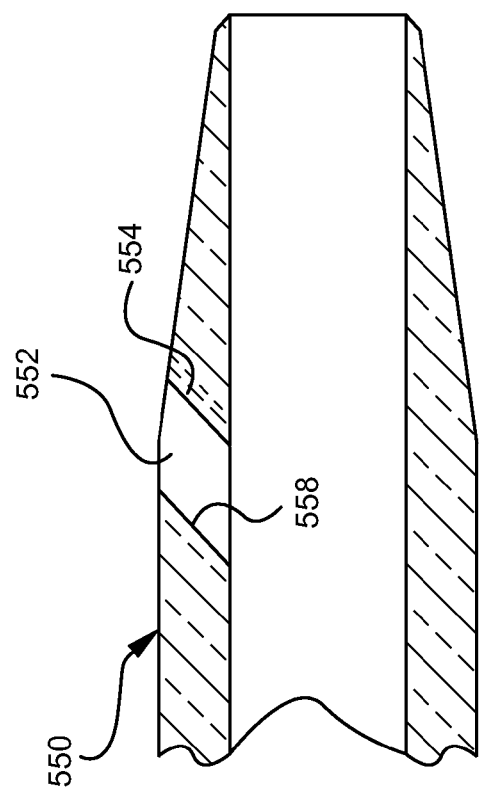
FIG. 11B is a cross-section side view of the catheter tip of FIG. 11A.
Figure 14:
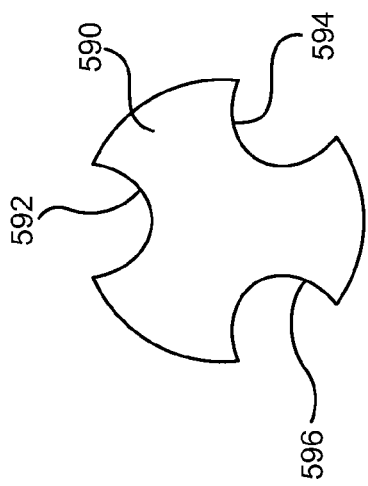
Figure 12:
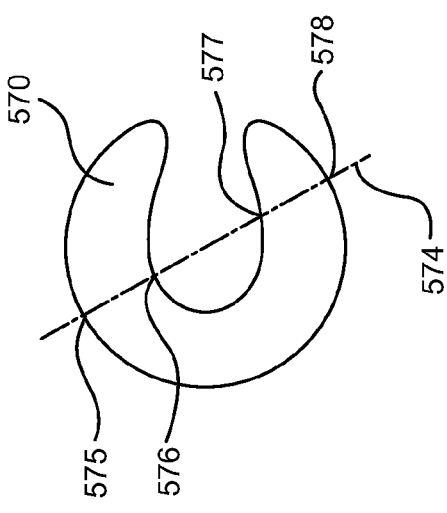
Figure 16:
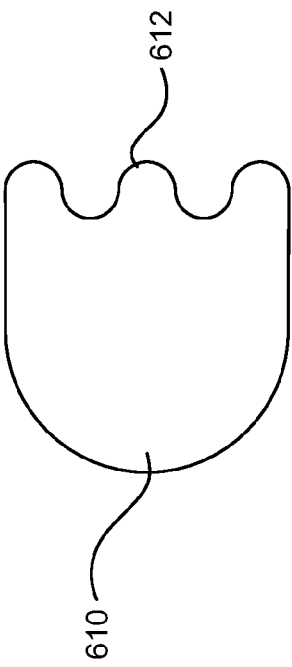

Referring now to FIGS. 11A-11B, a catheter 550 is illustrated, according to some embodiments, having a diffusion hole 552 with an inward projection 554 on the inner wall surface 558 of the hole 552. The inward projection 554 extends between the inner and the outer hole openings. Fluid flowing through the hole 552 has greater surface area than it would have when flowing through a circular hole, thus, the exiting jet will break up more quickly in the vein environment.

Referring now to FIGS. 12-16, which depict hole geometries having at least one inward projection. These structures project toward an inner portion of the hole, such that there exists a cross sectional area of the hole in which a straight line interposed over the cross section could cross the perimeter of the hole more than two times. This is illustrated in FIG. 12. Referring now to FIG. 12, which illustrates a cross section of a hole 570 having an inward projection. A line, which is not a structural component of the hole, and which is illustrated merely for illustration, is shown as crossing the perimeter of the hole at four points 575, 576, 577, and 578. Accordingly, structure 572 qualifies as an inward projection because the straight line 577 crosses the perimeter of the hole more than two times.

Figure 13:
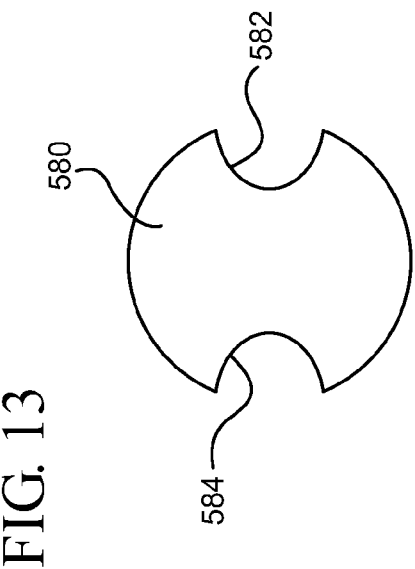
Figure 15:
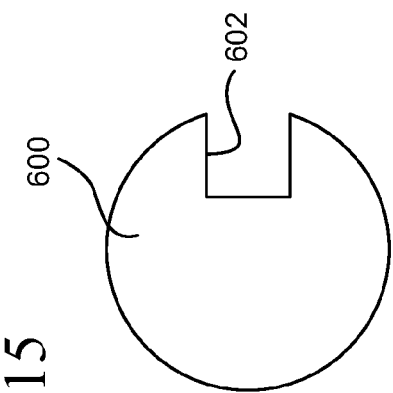

In some embodiments, as in FIG. 13, a hole 580 includes two inward projections 582 and 584. In other embodiments, as in FIG. 14, a hole 590 includes three inward projections 592, 594, and 596. In yet other embodiments, a hole includes more than three inward projections. As one inward projection increases the surface area of the resulting fluid stream, it follows that each increasing inward projection likewise increases the surface area. Accordingly, the number and dimensions of the inward projections disposed on a diffuser hole may be varied and adjusted to achieve a desired jet breakup, jet thinning, and jet slowing. Additionally, in some embodiments, as illustrated in FIG. 15, a hole 600 may include a non-round inward projection 602, such as square projection. Alternatively, in other embodiments, the inward projection is triangular, trapezoidal, rectangular, etc. Furthermore, in some embodiments, multiple inward projections 612 are disposed adjacent to one another or substantially adjacent to one another, such as those depicted on the hole 610 of in FIG. 16, which form a serrated edge of the hole.

Referring now to FIG. 17, an elongated diffuser hole 620 is illustrated as having a length 624 greater than a width 622. As referenced above, non-circular diffuser holes have greater surface area and thus fluid flowing therethrough has increased energy dissipating properties. However, diffuser holes with very substantial lengths in relation to the thickness of the peripheral catheter act as cuts within the catheter body that may weaken the catheter body. Accordingly, with peripheral catheters, one or more elongated diffuser hole may be included on the distal portion of the catheter body having a hole length 624 that is between 1.2-3.0 times the hole width 622. In other embodiments, the hole length is between 1.3-2.5 times the hole width. Still, in other embodiments, the hole length is between 1.4-2.2 times the hole width.

FIGS. 18-19 illustrates other elongated holes 630 and 640 having wedged extensions 6365 and 646, according to some embodiments. Specifically, FIG. 18 illustrates a hole 630 having a generally tear-drop shape, which facilitates insertion into a patient. The hole is elongated, having a length 636 and 632 that is generally greater than the width 634. The hole 630 includes a main hole portion 632 and a wedged extension 636, which includes two straight surfaces or semi-straight surfaces 635 and 637 extending from the main body portion 632 toward a point 638 away from the main body portion 632. In some embodiments, the hole 630 is oriented such that the point 638 of the wedge extension is on the proximal side of the hole. As the catheter is inserted through the skin of a patient, skin may naturally sink into the hole. As the catheter is advanced, the straight surfaces 635 and 637 gradually force skin out of the hole 630 and prevent skin snag that may otherwise occur if the proximal side of the hole comprises a large flat surface perpendicular to the direction of insertion. FIG. 19 depicts another tear-drop shape hole 640 having a rounded wedged extension 646, a main hole portion 644, and an hole width, according to some embodiments. The rounded wedged extension 646 decreases the overall length 644 and 646 of the hole 640 to increase the strength of the catheter body.

Referring now to FIG. 20, which illustrates a cross sectional view of a catheter 700 having a catheter body 702 comprising two diffuser holes 704 and 706. As illustrated, the two holes are oriented such that the fluid jet exiting the first hole 704 collides with the fluid jet exiting the second hole 706. Accordingly, the angles between the lumen and the first hole axis 708 is generally greater than the angle between the lumen and the second hole axis 710 such that the two axis orientations cause issuing fluid jets to collide. As these fluid jets collide, the force and orientation of each jet disrupts the other jet, dispersing the fluid, slowing the fluid, and/or causing turbulence within the resulting area of disrupted flow 716.

To achieve effective collisions, the location of collision may be closer to the catheter surface than the distance between the location of the holes on the catheter body 702 and a vein wall so that the impact actually occurs rather than the two jets impacting the vein wall. Accordingly, in some embodiments, the location of collision is configured to be a distance away from the outer surface of the catheter, wherein the distance is less than the overall thickness of the catheter body 702. In other embodiments, the distance is less than 150% the thickness of the catheter body 702. In other embodiments, the distance is less than 200% the thickness of the catheter body 702. In yet other embodiments, the distance is less than 300% the thickness of the catheter body 702. Still, in other embodiments, the distance is less than 50% the thickness of the catheter body 702. Furthermore, in some embodiments, the angle 718 between the first hole axis 708 and the second hole axis 710 is between ninety 15-90 degrees.

In some embodiments, flow can be broken by the collision of flow exiting a first diffuser hole and flow exiting a second, smaller diffuser hole. For example, one or more small diffuser holes is included on the catheter tip, and oriented so that fluid exiting therefrom collides with fluid exiting a larger diffuser hole. This way a greater number of holes can be included in the catheter tip without substantially weakening the tip with numerous holes of the same size.

Additionally, in some embodiments, fluid exiting a diffuser hole collides with fluid exiting two or more other diffuser holes. Referring now to FIG. 21, which illustrated a catheter 720 having three diffuser holes 722, 724, and 726, each having a hole axis 728, 730, and 732, respectively, which cause fluid exiting therefrom to collide with fluid exiting from one of the other holes. Thus, in some embodiments, the three holes are located in a generally triangular arrangement. In other embodiments, the three holes are located in a generally linear arrangement, such that a jet from an upstream hole collides with a jet from downstream hole and the resulting stream is further collided with by a jet from further downstream hole. Additionally, in some embodiments, the diffuser hole array configuration comprises an arrangement of holes oriented such that the exiting jets of nearly every hole collide with at least one jet exiting another hole. As such, the sum of the exiting jets will produce a fluid infusion with less impact energy and which poses a smaller risk to vessel walls.

In some embodiments, a single diffuser hole includes more than one flow breaking features. Examples of jet breaking features are described herein, including at least inward projections, wedged extensions, an elongated hole geometry, and hole axis orientations that result in collisions with other fluid jets. For example, in some embodiments, a hole includes an inward projection and has an axis orientation that collides with that of another hole. In addition, in some embodiments, the hole further includes a wedged extension. In other embodiments, other combinations of flow breaking features are combined to provide a less harmful, more effective catheter diffuser hole and diffuser hole array configuration.

From the foregoing, it will be seen that one or more flow breaking features can be included on one or more catheter diffuser holes on a catheter tip. The flow breaking feature can substantially breaks up, thins, or slows a jet of fluid exiting a hole so that the jet will lose speed more quickly within the vein and cause less damage to vessel walls. In particular, flow breaking features are particularly advantageous when used in rapid infusion therapy that uses highly infusant velocities to rapidly introduce a bolus of fluid into a patient through the catheter tip. During these procedures, one or more flow breaking features of a diffuser hole can increase infusion patient comfort, decrease patient pain, allow for greater infusion velocities, and prevent vessel damage.

EXAMPLES

To decrease the amount of contrast media required for a diagnosis, the concentration of contrast media per unit volume of blood needs to be increased by increasing the volumetric flow rate of the of contrast media without increasing the catheter tip velocity. The elements of the present invention achieve these required objectives, as demonstrated in the examples below.

Example 1

Tip Jet Velocity Comparison

The jet velocities at the tip of a standard catheter are in excess of 1,000 in/sec for a 5 ml/sec volumetric flow rate setting, which results in a large force applied to the vein wall of a patient. This force is treacherous for patients with non-optimal vein structure provisions increasing the likelihood of extravasation or intima damage with increasing flow rates.

Figure 5:
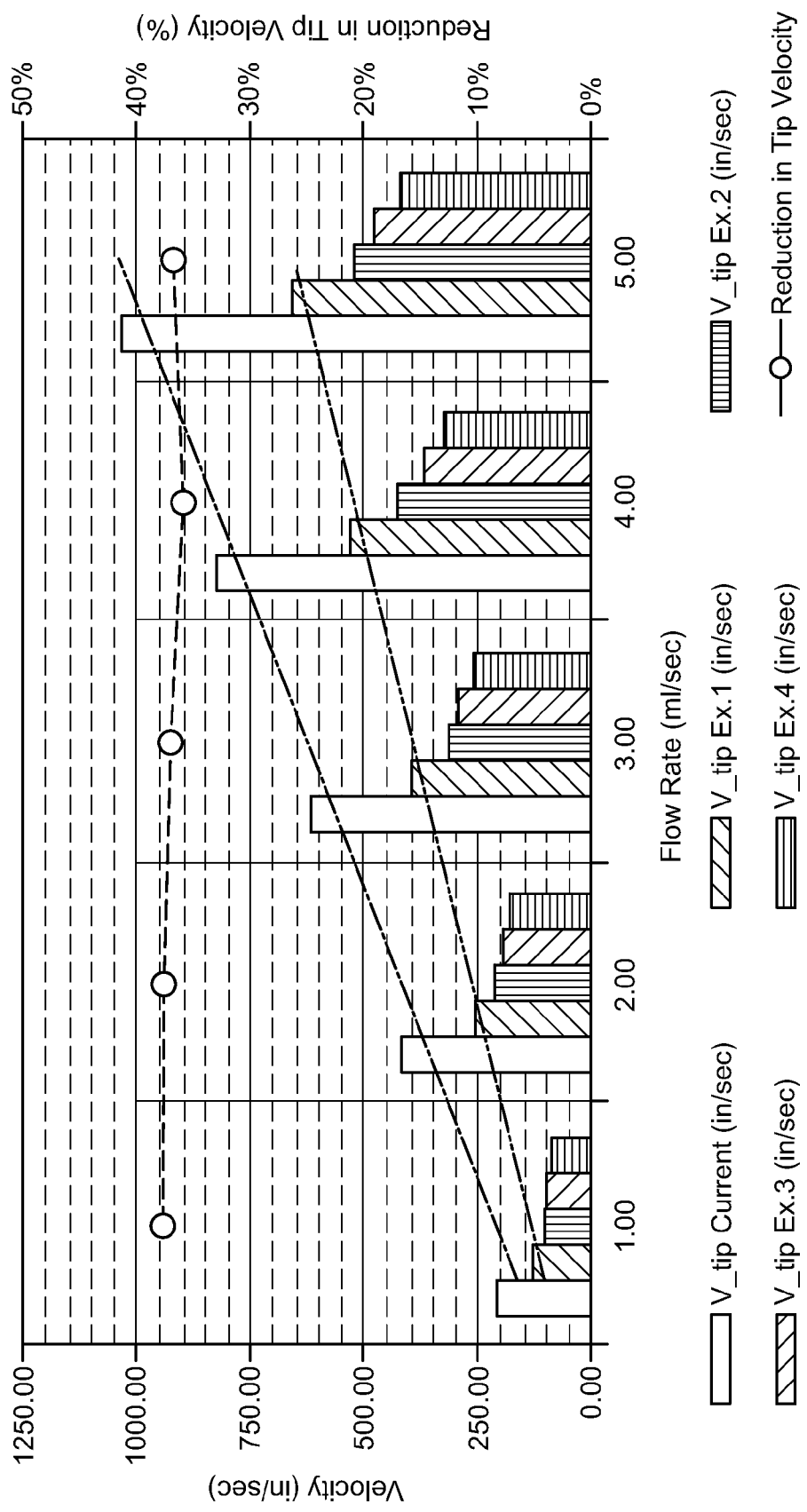
FIG. 5 is a graphical representation of jet tip velocities at various flow rates in accordance with representative embodiments of the present invention.

Jet tip velocities of a standard 22 GA×1.00" catheter (V_tip Current) were compared to a 22 GA×1.00" catheter (V_tip Ex. 1-V_tip Ex. 4) modified to include a plurality of diffusion holes, as described in connection with FIGS. 4A and 4B, above. Quadruplicate samples of the modified catheter were tested at flow rates of 1 ml/sec, 2 ml/sec, 3 ml/sec, 4 ml/sec, and 5 ml/sec. Tip jet velocity was then recorded for each sample and compared to the jet velocity of the standard catheter at each flow rate. The experiment demonstrated that the overall tip jet velocity of the modified catheter was decreased by 36% over the standard catheter. The results of the experiment are shown in FIG. 5.

Example 2

System Pressure Comparison

Internal pressures within an infusion system were compared between an infusion system using a standard 22

GA×1.00" catheter and an infusion system using a 22 GA×1.00" catheter (P_inj #1 and P_inj #2) modified to include a plurality of diffusion holes, as described in connection with FIGS. 4A and 4B, above.

Figure 6:
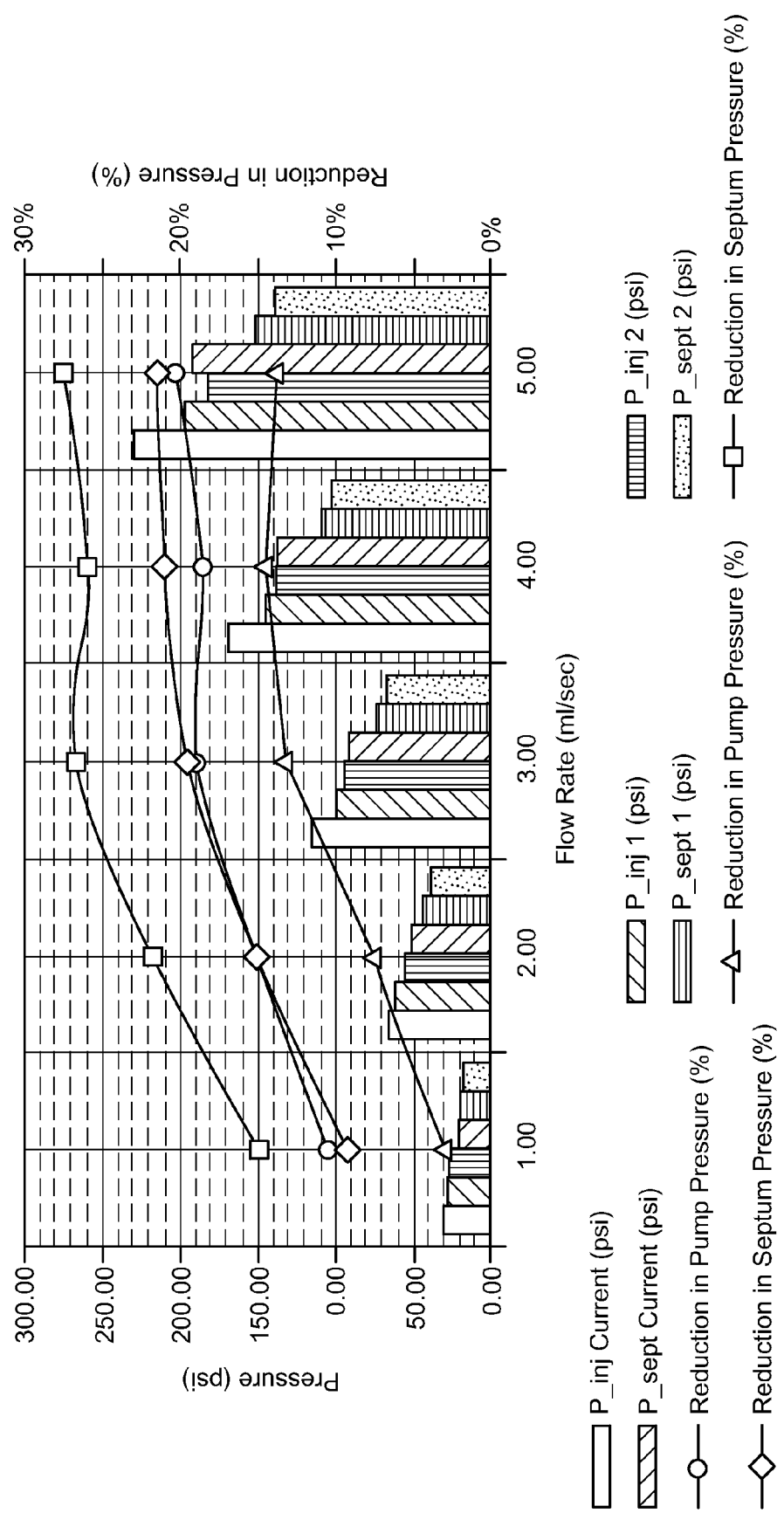
FIG. 6 is a graphical representation of system pressures at various flow rates in accordance with representative embodiments of the present invention.

System pressure was measured both within each infusion pump (P_inj Current, P_inj 1 and P_inj 2) and the inner lumen of each catheter (P_sept Current, P_sept 1 and P_sept 2). System pressure was tested and recorded at flow rates of 1 ml/sec, 2 ml/sec, 3 ml/sec, 4 ml/sec, and 5 ml/sec. System pressures at each flow rate where then graphed, as shown in FIG. 6.

The results of the experiment demonstrate an increase in the volumetric flow rate by decreasing system pressure by nearly 30%, with the greatest reduction in pressure being shown within the lumen of the modified catheters.

Example 3

Computational Fluid Dynamic Analysis

Computation fluid dynamic analysis was conducted on a standard 22 GA×1.00" catheter modified to include a plurality of diffusion holes bored approximately 45° relative to the inner wall surface of the catheter. The analysis revealed an addition 6% diversion of bulk flow from the main stream into the diffusion holes, as compared to a standard 22 GA×1.00" catheter having a plurality of diffusion holes bored 90° relative to the inner wall surface of the catheter. The analysis further revealed a significant increase in fluid flow 492 through the cross section of the diffusion hole 450, as compared to the straight holes of the standard catheter. While the diffusion holes 450 of the present invention did show a slight recirculation eddy 494, the recirculation eddy 494 was significantly weaker as compared to the circulation eddy 392 of the standard catheter. A representative rendering of the fluid flow 492 is shown in FIG. 4B.

Example 4

Catheter Stabilization and Vein Centering

In standard peripheral intravenous catheters, the inner lumen of the catheter tapers towards the tip of the catheter resulting in a recoil force as an infusant accelerates through the constriction. This force is akin to the force felt when holding a fire hose. Like a fire hose, a catheter tip under the compressive recoil force is unstable and can oscillate violently within the vein (also known as catheter whip) causing vein damage, as previously discussed. If enough infusant is turned from the axial direction through diffusion holes, then the recoil force will become negative and actually pull the catheter tip into tension; the tensioned state of the catheter tip providing great stability to the inserted catheter. Therefore, in some embodiments the bore angle is strategically selected to balance between increased flow through the diffusion holes and decreased recoil force on the catheter tip by reducing the axial direction of infusant flowing through the diffusion holes.

The bore angle further affects the positioning of the catheter within the vein. For example, when inserted in to a vein the venous catheter generally extends through the skin and into the vein at approximately 30°. As such, the tip of the venous catheter commonly contacts or rests against the inner wall of the vein opposite the insertion site of the catheter. As fluid flow increases, high jet velocity from the catheter tip is exerted directly on the inner wall of the vein. However, when the tip of the venous catheter is modified to include diffusion ports, the diverted infusant that issues from the diffusion ports pushes the catheter tip away from the vein wall resulting in a centralized position of the catheter tip within the vein. Thus, the jet velocity from the tip is directed into the fluid stream of the vein rather than into the vein wall.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A peripheral catheter, comprising:
   a catheter body having a proximal end, a distal end, a lumen extending between the proximal and distal ends, and a distal lumen, the catheter body further having a truncated length sufficient to access a peripheral vein of a patient;
   at least one hole positioned on the distal end of the catheter body, the hole being formed through a wall thickness of the catheter body and in communication with the lumen, the at least one hole having an inner wall surface and an inner portion; and
   an inward projection on the inner wall surface of the at least one hole and extending into the inner portion.

2. The peripheral catheter of claim 1, wherein the at least one hole includes at least two holes, the first hole having a first hole central axis defining a first vector through the first hole, the second hole having a second hole central axis defining a second vector through the second hole, the first vector converging with the second vector at a point external to the lumen of the catheter body.

3. The peripheral catheter of claim 1, wherein the at least one hole comprises a distal end and a proximal end, wherein the distal end is generally round and the proximal end is tapered.

4. The peripheral catheter of claim 1, wherein the at least one hole is substantially tear-drop shape.

5. The peripheral catheter of claim 1, wherein the at least one hole has an elongated geometry.

6. A peripheral catheter, comprising:
   a catheter body of a predetermined wall thickness, the catheter body member having a proximal end, a distal end, a lumen extending between the proximal and distal ends, and a distal lumen opening, the catheter body further having a truncated length sufficient to access a peripheral vein of a patient; and
   a hole positioned on the distal end of the catheter body, the hole being formed through the wall thickness of the catheter body and in communication with the lumen, the hole having an inner portion and further comprising a distal end and a proximal end, wherein the distal end is generally round and the proximal end is tapered.

7. A peripheral catheter of claim 6, further comprising an inward projection disposed on an inner wall surface of the hole and extending into the inner portion of the hole.

8. A peripheral catheter of claim 6, wherein the hole is an elongated hole.

9. A peripheral catheter of claim 6, wherein a surface area of an outer opening of the hole is less than a surface area of an inner opening of the hole.

10. A peripheral catheter of claim 6, wherein a surface area of the hole is less than a surface area of the distal lumen opening.

11. A peripheral catheter of claim 6, wherein an angle between a distal inner wall surface of the hole and a central axis of the catheter is less than an angle between a proximal inner wall surface of the hole and the central axis of the catheter.

12. A peripheral catheter of claim 6, wherein the hole is at least partially disposed on a tapered tip of the distal end of the catheter body.

13. A peripheral catheter of claim 6, wherein the catheter body comprises a diameter that is less than or equal to a fourteen gauge catheter.

14. A peripheral catheter, comprising: a catheter body having a proximal end, a distal end, a lumen extending between the proximal and distal ends, and a distal lumen, the catheter body further having a truncated length sufficient to access a peripheral vein of a patient; a plurality of holes positioned on the distal end of the catheter body, the plurality of holes being formed through a wall thickness of the catheter body and in communication with the lumen, the plurality of holes each having an inner wall surface and an inner portion, the plurality of holes each having a distal end and a proximal end, wherein the distal end is generally round and the proximal end is tapered; and an inward projection on the inner wall surface of one or more of the plurality of holes and extending into the inner portion.

15. A peripheral catheter of claim 14, wherein plurality of holes are elongated holes.

16. A peripheral catheter of claim 14, wherein a surface area of an outer opening of each of the plurality of holes is less than a surface area of an inner opening of each of the plurality of holes.

17. A peripheral catheter of claim 14, wherein a surface area of each of the plurality of hole is less than a surface area of the distal lumen opening.

18. A peripheral catheter of claim 14, wherein one or more of the plurality of holes is at least partially disposed on a tapered tip of the distal end of the catheter body.

19. A peripheral catheter of claim 1, wherein a surface area of an outer opening of the at least one hole is less than a surface area of an inner opening of the at least one hole.

20. A peripheral catheter of claim 1, wherein a surface area of the at least one hole is less than a surface area of the distal lumen opening.

* * * * *